(12) United States Patent  
Bassett et al.

(10) Patent No.: US 9,554,877 B2
(45) Date of Patent: Jan. 31, 2017

(54) DENTAL REGENERATIVE DEVICE MADE OF POROUS METAL

(71) Applicant: Zimmer, Inc., Warsaw, IN (US)

(72) Inventors: Jeffrey Bassett, Vista, CA (US); Leonard Conner, Parsippany, NJ (US); Edward M. Willis, Hoboken, NJ (US); Ken Varner, Floral Park, NY (US); Michael Scott Collins, San Marcos, CA (US)

(73) Assignee: Zimmer, Inc., Warsaw, IN (US)

( * ) Notice: Subject to any disclaimer, the term of this patent is extended or adjusted under 35 U.S.C. 154(b) by 88 days.

(21) Appl. No.: 14/040,414

(22) Filed: Sep. 27, 2013

(65) Prior Publication Data

US 2014/0099601 A1    Apr. 10, 2014

Related U.S. Application Data

(63) Continuation-in-part of application No. 13/954,051, filed on Jul. 30, 2013.

(60) Provisional application No. 61/677,955, filed on Jul. 31, 2012.

(51) Int. Cl.
*A61C 8/02* (2006.01)
*A61K 6/04* (2006.01)

(52) U.S. Cl.
CPC ............. *A61C 8/0006* (2013.01); *A61K 6/04* (2013.01)

(58) Field of Classification Search
CPC ................................ A61C 8/0006; A61K 6/04
USPC .................... 433/201.1, 173–176; 623/16.11
See application file for complete search history.

(56) References Cited

U.S. PATENT DOCUMENTS

| | | | |
|---|---|---|---|
| 2,112,007 A | | 3/1938 | Adams |
| 3,514,489 A | * | 5/1970 | Lemberg ........................ 568/446 |
| 3,579,829 A | * | 5/1971 | Sampson ....................... 433/158 |
| 3,855,638 A | * | 12/1974 | Pilliar ........................ 623/23.55 |
| 3,952,414 A | | 4/1976 | Shovers et al. |
| 4,073,999 A | * | 2/1978 | Bryan et al. ................ 428/312.8 |
| 4,121,340 A | * | 10/1978 | Patrick .......................... 433/176 |
| 4,379,694 A | * | 4/1983 | Riess .......................... 433/201.1 |
| 4,521,192 A | * | 6/1985 | Linkow ......................... 433/173 |

(Continued)

OTHER PUBLICATIONS

"Zimmer CurV Pre-Shaped Collagen Membrane, The Latest in Ridge Augmentation Takes Shape", Zimmer Dental, (2011), 2 pgs.

(Continued)

*Primary Examiner* — Cris L Rodriguez
*Assistant Examiner* — Hao D Mai
(74) *Attorney, Agent, or Firm* — Schwegman Lundberg & Woessner, P.A.

(57) ABSTRACT

A regenerative device can include a first side section, a second side section, and a top section extending between and connecting the first side section and the second side section. The top section and the first and second side sections can each be formed from a porous material that retains its structure after implantation in the patient. The regenerative device can be used for ridge augmentation of a maxilla or a mandible. The top section can include an opening configured for receiving an implant. The porous material can be permanently implanted in the mouth and promote bone regeneration or ridge augmentation. One or both of the first and second side sections of the device can include one or more openings or apertures for receiving a fastener to secure the device to the alveolar ridge.

11 Claims, 15 Drawing Sheets

(56) References Cited

U.S. PATENT DOCUMENTS

| | | | |
|---|---|---|---|
| 4,531,916 A * | 7/1985 | Scantlebury et al. | 433/173 |
| 4,702,697 A * | 10/1987 | Linkow | 433/173 |
| 4,957,439 A * | 9/1990 | Shoher et al. | 433/180 |
| 4,964,801 A * | 10/1990 | Kawahara et al. | 433/173 |
| 5,032,445 A * | 7/1991 | Scantlebury et al. | 428/158 |
| 5,052,930 A * | 10/1991 | Lodde et al. | 433/173 |
| 5,084,051 A * | 1/1992 | Tormala et al. | 606/77 |
| 5,108,432 A * | 4/1992 | Gustavson | 623/23.54 |
| 5,201,736 A * | 4/1993 | Strauss | 606/285 |
| D336,683 S * | 6/1993 | Inoue et al. | D24/156 |
| 5,222,987 A * | 6/1993 | Jones | 623/66.1 |
| 5,282,861 A | 2/1994 | Kaplan | |
| 5,306,149 A * | 4/1994 | Schmid et al. | 433/173 |
| 5,360,341 A * | 11/1994 | Abramowitz | 433/215 |
| 5,372,503 A | 12/1994 | Elia | |
| 5,380,328 A * | 1/1995 | Morgan | 606/70 |
| 5,397,235 A | 3/1995 | Elia | |
| 5,513,989 A * | 5/1996 | Crisio | 433/176 |
| 5,759,033 A | 6/1998 | Elia | |
| 5,769,637 A * | 6/1998 | Morgan | 433/176 |
| 5,769,898 A | 6/1998 | Jisander | |
| 5,906,489 A * | 5/1999 | Khazzam et al. | 433/176 |
| 6,030,218 A * | 2/2000 | Robinson | A61C 8/0006 433/173 |
| 6,050,819 A * | 4/2000 | Robinson | A61C 8/0006 433/173 |
| 6,080,161 A | 6/2000 | Eaves, III et al. | |
| 6,328,765 B1 * | 12/2001 | Hardwick et al. | 623/23.72 |
| 6,382,975 B1 | 5/2002 | Poirier | |
| 6,402,518 B1 | 6/2002 | Ashman | |
| 6,409,764 B1 * | 6/2002 | White et al. | 623/16.11 |
| 6,840,770 B2 | 1/2005 | McDevitt | |
| 7,887,587 B2 * | 2/2011 | Griffiths et al. | 623/16.11 |
| 8,177,557 B2 * | 5/2012 | Delmonico et al. | 433/180 |
| 8,202,089 B2 * | 6/2012 | Dacremont | 433/173 |
| 8,357,201 B2 | 1/2013 | Mayer et al. | |
| 8,485,820 B1 * | 7/2013 | Ali | 433/173 |
| 2001/0012606 A1 | 8/2001 | Unger | |
| 2002/0110785 A1 | 8/2002 | Ashman | |
| 2003/0036801 A1 | 2/2003 | Schwartz et al. | |
| 2003/0125750 A1 | 7/2003 | Zwirnmann et al. | |
| 2004/0152046 A1 * | 8/2004 | Minoretti | A61B 17/663 433/173 |
| 2005/0033427 A1 * | 2/2005 | Freilich | A61B 17/68 623/16.11 |
| 2005/0159754 A1 * | 7/2005 | Odrich | 606/86 |
| 2005/0273165 A1 * | 12/2005 | Griffiths | A61L 31/16 623/16.11 |
| 2006/0008773 A1 * | 1/2006 | Liao | 433/173 |
| 2006/0166169 A1 * | 7/2006 | Dawood | A61B 17/666 433/174 |
| 2006/0287732 A1 | 12/2006 | Pezeshkian | |
| 2006/0292523 A1 * | 12/2006 | Elian | 433/173 |
| 2007/0231364 A1 * | 10/2007 | Nishimoto et al. | 424/424 |
| 2007/0269483 A1 | 11/2007 | Elia | |
| 2007/0269769 A1 * | 11/2007 | Marchesi | 433/215 |
| 2008/0095709 A1 * | 4/2008 | Ella | 424/9.1 |
| 2009/0048145 A1 | 2/2009 | Hellerbrand et al. | |
| 2009/0198284 A1 | 8/2009 | Henry | |
| 2010/0023057 A1 | 1/2010 | Aeschlimann et al. | |
| 2010/0036441 A1 | 2/2010 | Procter | |
| 2010/0161061 A1 * | 6/2010 | Hunt | 623/17.16 |
| 2010/0256773 A1 * | 10/2010 | Thijs et al. | 623/23.55 |
| 2011/0008754 A1 * | 1/2011 | Bassett et al. | 433/175 |
| 2011/0035024 A1 | 2/2011 | Malmquist et al. | |
| 2011/0224739 A1 | 9/2011 | Wieland et al. | |
| 2012/0156644 A1 * | 6/2012 | McKay | 433/173 |
| 2012/0178042 A1 | 7/2012 | Brodkin et al. | |
| 2012/0244498 A1 | 9/2012 | Hall | |
| 2013/0090742 A1 | 4/2013 | Boiangiu | |
| 2013/0123928 A1 | 5/2013 | Mayer et al. | |
| 2013/0164707 A1 * | 6/2013 | Ali | 433/173 |
| 2013/0274819 A1 * | 10/2013 | Horvath | 606/86 R |
| 2013/0280675 A1 * | 10/2013 | Ali | 433/173 |
| 2013/0288200 A1 | 10/2013 | Battula et al. | |
| 2014/0038132 A1 * | 2/2014 | Willis et al. | 433/173 |
| 2014/0272778 A1 * | 9/2014 | Llop | A61C 8/0089 433/72 |
| 2016/0038255 A1 * | 2/2016 | Llop | A61C 8/0089 433/75 |

OTHER PUBLICATIONS

"Zimmer CurV Pre-Shaped Collagen Membrane, The Latest in Ridge Augmentation Takes Shape", Surgical Technique Guide—Anterior, Zimmer Dental, (2012), 15 pgs.

"U.S. Appl. No. 13/838,341, Examiner Interview Summary mailed Jan. 6, 2014", 4 pgs.

"U.S. Appl. No. 13/838,341, Final Office Action mailed Feb. 26, 2014", 11 pgs.

"U.S. Appl. No. 13/838,341, Non Final Office Action mailed Nov. 27, 2013", 14 pgs.

"U.S. Appl. No. 13/838,341, Response filed Jan. 21, 2014 to Non-Final Office Action mailed Nov. 27, 2013", 20 pgs.

"U.S. Appl. No. 13/954,051, Non Final Office Action mailed Mar. 26, 2014", 8 pgs.

"U.S. Appl. No. 13/954,051, Response filed Jun. 26, 2014 to Non Final Office Action mailed Mar. 26, 2014", 15 pgs.

"U.S. Appl. No. 13/838,341, Response filed Feb. 26, 2015 to Non-Final Office Action mailed Sep. 30, 2014", 11 pgs.

"U.S. Appl. No. 13/954,041, Response filed Feb. 4, 2015 to Final Office Action mailed Dec. 4, 2014", 11 pgs.

"U.S. Appl. No. 13/838,341, Advisory Action mailed Jun. 12, 2015", 3 pgs.

"U.S. Appl. No. 13/838,341, Final Office Action mailed Mar. 24, 2015", 13 pgs.

"U.S. Appl. No. 13/838,341, Non Final Office Action mailed Dec. 17, 2015", 16 pgs.

"U.S. Appl. No, 13/838,341, Response filed May 26, 2015 to Final Office Action mailed Mar. 24, 2015", 12 pgs.

* cited by examiner

DENTAL REGENERATIVE DEVICE MADE OF POROUS METAL

CLAIM OF PRIORITY

This application is a continuation-in-part of U.S. patent application Ser. No. 13/954,051, filed on Jul. 30, 2013 and entitled DENTAL REGENERATIVE DEVICE MADE OF POROUS METAL, which claims the benefit of U.S. Provisional Patent Application Ser. No. 61/677,955, entitled "DENTAL REGENERATIVE DEVICE MADE OF POROUS METAL", and filed on Jul. 31, 2012, the benefit of priority of which is claimed hereby, and each of which is incorporated by reference herein in its entirety.

TECHNICAL FIELD

The present patent application relates to a dental procedure and more particularly, to an apparatus and method of regenerating bone of the alveolar ridge.

BACKGROUND

Dental implants may be used for the replacement of all, or a portion of, a patient's teeth. Following the extraction of one or more teeth, the bone that forms the maxilla or the mandible may resorb in the area where the one or more teeth were removed. The resulting loss of bone may make it difficult to secure a dental implant in the patient's mouth where the one or more extracted teeth were previously positioned. As such, various materials may be used to restore the bone prior to, or as part of, a procedure to place the implant(s) inside the patient's mouth.

In some cases, a titanium mesh material can be used in combination with a grafting material, in order to help promote bone growth. In addition to or as an alternative to a metal material, a resorbable material can be used to regenerate bone.

OVERVIEW

The present inventors have recognized, among other things, that there is an opportunity for a regenerative device and method that can maintain its structure and space in the mouth over time, while promoting bone growth. More particularly, the present inventors have recognized that a device formed from a porous material can retain its shape and structure after implantation in the mouth and can be used to regenerate bone of the alveolar ridge vertically and/or horizontally.

To better illustrate the dental regenerative device and methods disclosed herein, a non-limiting list of examples is provided here:

In an example, a regenerative device, configured for placement on an alveolar ridge in a maxilla or a mandible of a patient, can comprise a first side section, a second side section, and a top section extending between and connecting the first and second side sections. The top section and the first and second side sections can each be formed from a porous material that is configured to retain its structure after implantation in a patient. The top section can include one or more openings formed in the top section and configured for receiving an implant. The device can be optionally configured such that the top section, the first side section, and the second side section form an elongated arch. The one or more openings can optionally extend into at least one of a portion of the first side section and a portion of the second side section. The regenerative device can optionally have a curvature along at least a portion of an overall length of the regenerative device such that the regenerative device is configured to conform with a shape of a maxilla or a mandible of the patient. The regenerative device can optionally be configured such that an end of the first side section extends past an end of the second side section to form an attachment portion. The attachment portion can be configured for attachment to the alveolar ridge. The porous material can optionally be a porous tantalum structure.

In an example, a ridge augmentation device can comprise an elongated arch having a first side portion, a second side portion, and a top portion disposed between the first and second side portions. The elongated arch can be formed of a porous metal and can be configured to be secured to an alveolar ridge of a patient. The top portion can include one or more openings configured for receiving an implant. The one or more openings can optionally extend into a portion of the first side section and a portion of the second side section. The top portion can optionally include a plurality of arch segments, and the one or more openings can be defined between each pair of adjacent arch segments. At least one of the arch segments can optionally include a groove configured to create a detachment point for a selected portion of the ridge augmentation device to be detachable from a remaining portion of the ridge augmentation device.

In an example, a porous structure configured for use as one or more ridge augmentation devices for placement in a maxilla or a mandible of a patient, can comprise a first side section, a second side section, and a top section extending between and connecting the first side section and the second side section. The top section can have a curved shape and can define a plurality of arch segments, wherein an opening is defined between each pair of adjacent arch segments and is configured for receiving an implant. At least one of the arch segments can include a groove configured to allow a selected portion of the porous structure to be detached for use as a ridge augmentation device. The porous structure can optionally be generally linear along an overall length of the porous structure or the porous structure can optionally have a curvature along at least a portion of the overall length. The first side section can optionally include a plurality of apertures, each aperture configured for receiving a fastener to attach the porous structure or a portion thereof to an alveolar ridge of a patient. The plurality of arch segments can optionally have a generally equal height to one another or at least one of the arch segments can optionally have a different height than at least one of the other arch segments. The porous structure can optionally be tantalum.

In an example, a method of performing ridge augmentation of a maxilla or a mandible of a patent to regenerate bone can include exposing a portion of the bone that forms the alveolar ridge in the maxilla or the mandible of the patient by cutting through tissue covering the bone and securing a regenerative device to the exposed portion of the bone. The regenerative device can include an opening configured for receiving an implant and formed of a porous metal that retains its structure after implantation in the maxilla or the mandible. The method can include closing the tissue around the exposed portion of the bone and the regenerative device. The method can optionally further comprise placing a membrane over the regenerative device, prior to closing the surrounding tissue around the exposed portion of the bone and the regenerative device, wherein the membrane is formed of a material that prevents soft tissue from growing into the porous metal of the regenerative device. The method can optionally further comprise selecting an appropriate size and shape of the regenerative device, prior to securing the regenerative device to the bone, which can optionally include separating the regenerative device from an elongated piece of porous metal having grooves formed therein to create points of detachment from the elongated piece.

These and other examples and features of the present regenerative devices, kits, and methods will be set forth in part in the following Detailed Description. This overview is intended to provide a summary of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
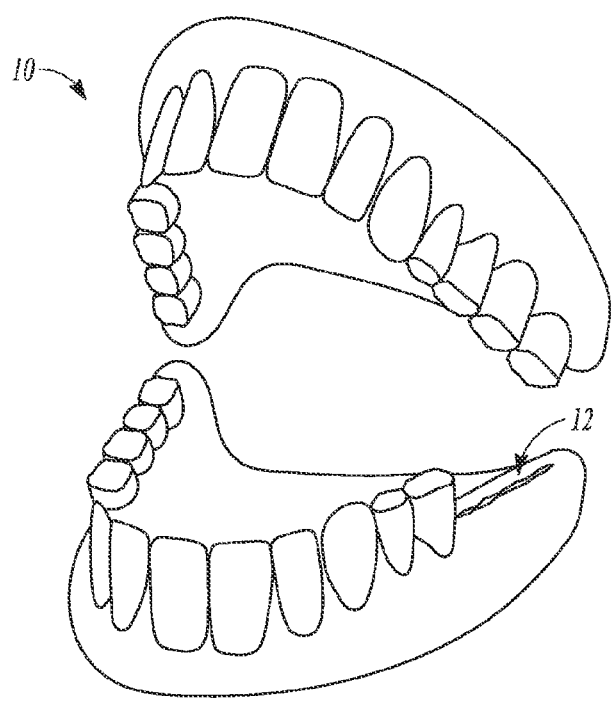
FIG. 1 is a perspective view of a mouth, including an area of the mandible where teeth have been removed.

FIG. 1 shows an inside of a patient's mouth 10 after the removal of one or more teeth from an area 12 in the mouth 10. The teeth may have been removed, for example, due to extensive decay or other damage.

Figure 2:
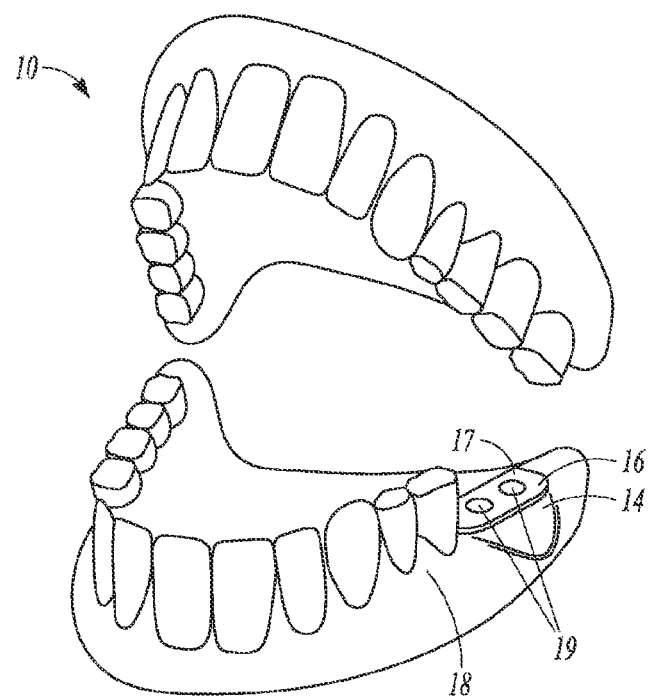
FIG. 2 is a perspective view of the mouth of FIG. 1 after the tissue has been cut, exposing a portion of the bone forming the alveolar ridge of the mandible.

FIG. 2 shows the mouth 10 after a portion of tissue 14 has been cut and then pulled back, exposing a portion of bone 16 that forms an alveolar ridge 17 in the mouth 10. More specifically, the bone 16 is part of the alveolar ridge 17 that forms a mandible 18, or lower jaw, of the mouth 10. Holes 19 are shown in FIG. 2 where the one or more removed teeth previously resided. Particularly, FIG. 2 depicts two holes 19 that correspond with two teeth that have been removed from the mandible 18 of the mouth 10. However, more or less teeth can be removed from the mandible 18 in a similar procedure. Furthermore, one or more teeth can similarly be removed from the maxilla 22, or upper jaw, of the mouth 10.

Figure 3:
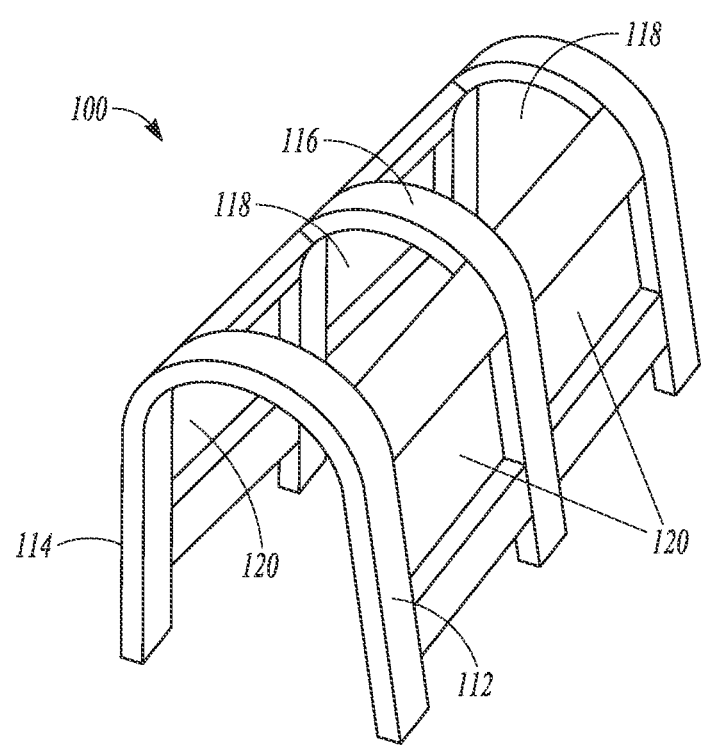
FIG. 3 is a perspective view of an example of a dental regenerative device in accordance with the present application.

FIG. 3 shows an example of a dental regenerative device 100 that can be implanted inside the mouth 10 in an area, similar to the area 12 shown in FIG. 1, where one or more teeth have been removed. Once the one or more teeth have been removed from the mouth 10, bone absorption can occur in the surrounding area, and in some cases, such bone absorption can occur rapidly. The dental regenerative device 100 can be used to facilitate regrowth of the bone 16 in the area 12. For example, the regenerative device 100 can be used for vertical bone growth (to regain or increase a height of the bone 16) and/or horizontal bone growth. This bone growth or bone regrowth can also be described using alternative terms, such as, for example, ridge augmentation or bone augmentation.

The dental regenerative device 100 can be formed from at least one material that can allow the dental regenerative device 100 to maintain a desired shape inside the mouth 10. In an example, the dental regenerative device 100 can be formed from a biocompatible, rigid, porous material that is able to retain its shape and structure long after implantation in the mouth 10. Because the device 100 can be formed of a rigid material, the device 100 can be implanted inside the mouth 10 without a supplemental support structure. However, in examples, the device 100 can be paired with a supplemental support structure if desired. This is in contrast to other designs, which require a support material to be used in combination with the regenerative material, in which case, the support material may need to be removed from the mouth in a subsequent surgery.

In an example, the dental regenerative device 100 can be formed of a porous structure, such as to facilitate bone ingrowth or regrowth. A porous biomaterial can be useful as a bone substitute, and can have a porosity as low as 55%, 65%, or 75%, or as high as 80%, 85%, or 90%, or within any range defined by any of the foregoing values. In an example, the porous structure can include or can be formed of a material produced using Trabecular Metal™ Technology, generally available from Zimmer, Inc. of Warsaw, Ind.

Trabecular Metal™ is a trademark of Zimmer, Inc. Such a material can be formed using a foamed polymer (such as polyurethane, as one example) that can be reduced to a reticulated vitreous carbon foam substrate or skeleton. The carbon skeleton can be infiltrated and coated with a first layer of biocompatible metal, such as tantalum, to produce a low density material, and then plated with a second layer of tantalum to produce a high density material. The metal can be deposited on the carbon substrate by a chemical vapor deposition (CVD) process, such as in the manner disclosed in detail in U.S. Pat. No. 5,282,861, the disclosure of which is incorporated herein by reference. One or more other metals, e.g., in addition to tantalum, including alloys thereof, can be used, such as, for example, niobium.

Generally, the porous structure can include a large plurality of ligaments defining open spaces there between, with each ligament generally including a carbon core covered by a thin film of metal, such as tantalum, for example. The open spaces between the ligaments can form a matrix of continuous channels, such as having no dead ends, such as to permit uninhibited growth of cancellous bone through the porous tantalum structure. The porous structure can include up to 75%-85% or more void space therein. In an example, a porous tantalum structure can provide a lightweight, strong porous structure that can be substantially uniform and consistent in composition, and that can closely resemble the structure of natural cancellous bone, which can thereby provide a matrix into which cancellous bone can grow. The porous tantalum structure can be made in a density selected from a variety of densities, such as to selectively tailor the structure for a particular application. The porous tantalum can be fabricated to permit selecting virtually any desired porosity and pore size, and can thus be matched with the surrounding natural bone, such as to provide an improved matrix for bone ingrowth and mineralization.

Because the dental regenerative device 100 can be formed of a porous material, bone can grow into and through the device 100. The device 100 can remain inside the mouth of the patient for a long period or indefinitely.

In an example, the dental regenerative device 100 can be used with a membrane. After the dental regenerative device 100 is implanted inside the mouth, the membrane can be placed over the dental regenerative device 100 during the same surgery or during a subsequent surgery. The membrane can be used as a barrier to prevent soft tissue growth through the dental regenerative device 100 in order to enable bone growth through the device 100. The membrane can be formed of any material(s) that can act as a soft tissue barrier, and such materials can include, for example, collagen and pericardium. The membrane can be a temporary membrane that can be removed from the body in a later surgery, or the membrane can be formed from a resorbable material, such as collagen.

The dental regenerative device 100 can include a first side section 112, a second side section 114, and a top section 116 disposed between the first side section 112 and the second side section 114. The dental regenerative device 100 can be a continuous piece which can include the first 112 and second 114 side sections and the top section 116. At least a portion of the first 112 and second 114 side sections can be generally parallel to one another, or the first 112 and second 114 side sections can extend in non-parallel planes. The top section 116 can be curved, as shown in FIG. 3, such that the top section 116 and the first 112 and second 114 side sections form an elongated arch.

The top section 116 can include one or more windows or openings 118 configured to receive an implant, as described below. Thus, although FIG. 3 depicts two openings 118 in the top section 116, more or less than the two openings 118 can be provided. The openings 118 can be generally rectangular in shape, as shown in FIG. 3, or the openings 118 can have a different shape, such as, for example, a circular shape or an irregular shape. The size of the openings 118 can also be larger or smaller than the size of the openings shown in FIG. 3. In addition to or as an alternative to receiving an implant(s), the openings 118 can be configured to reduce or minimize an overall weight of the dental regenerative device 100, as well as the total amount of material used to form the dental regenerative device 100.

The openings 118 can be structured to receive an implant, which can typically include a screw or a shaft that can be placed into a bore formed in the bone 16 and used to support a dental prosthesis. Common materials for dental implants can include, for example, titanium or an alloy thereof. A first portion of the implant can be configured for implantation within the bone 16 and a second portion of the implant can be configured to extend above the gum line of the mouth 10. The second portion of the implant can engage with or receive a dental prosthesis, such as, for example, a crown or a bridge. When placing the dental regenerative device 100 inside the mouth, the openings 118 on the top section 116 can thus be aligned with the desired implant locations inside the mouth 10.

Because there are two openings 118, as shown in FIG. 3, at least two implants can be used with the dental regenerative device 100, with one implant placed inside each opening 118. Alternatively, because each of the openings 118 occupies a significant amount of the top section 116 in the example shown in FIG. 3, it can be possible to place two or more implants in each of openings 118, depending, at least in part, on a size of the openings 118 relative to the size of the implants. As discussed further below, the size and shape of the openings 118 can vary.

The implant(s) can be 'loaded' or placed inside the mouth 10 at the same time that the dental regenerative device 100 is implanted inside the mouth. The excess space around the implant and the dental regenerative device 100 can be packed with bone graft and/or bone filler. Alternatively, the implant(s) can be loaded as a part of a separate surgery that takes place at a later date following implantation of the dental regenerative device 100, such as to give the bone 16 time to regenerate around and through the dental regenerative device 100 before loading the implant(s). For example, loading of the implant at a later date can allow the bone 16 time to regenerate vertically through the use of the dental regenerative device 100.

Figure 3A:
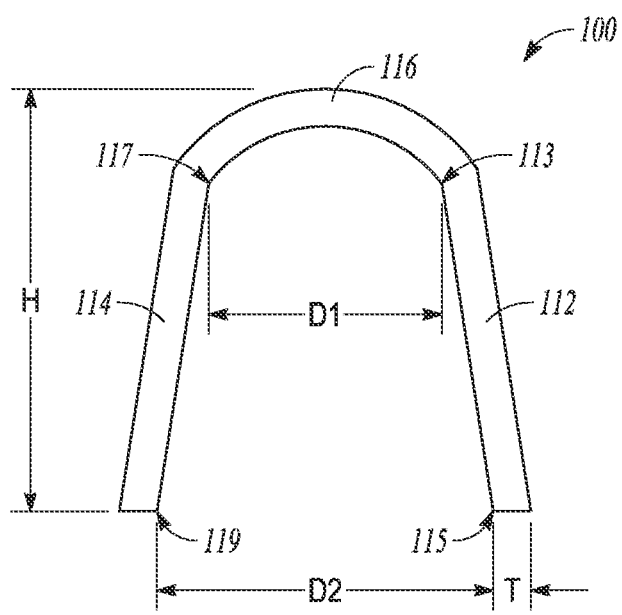
FIG. 3A is an end view of the dental regenerative device of FIG. 3.
Figure 3B:
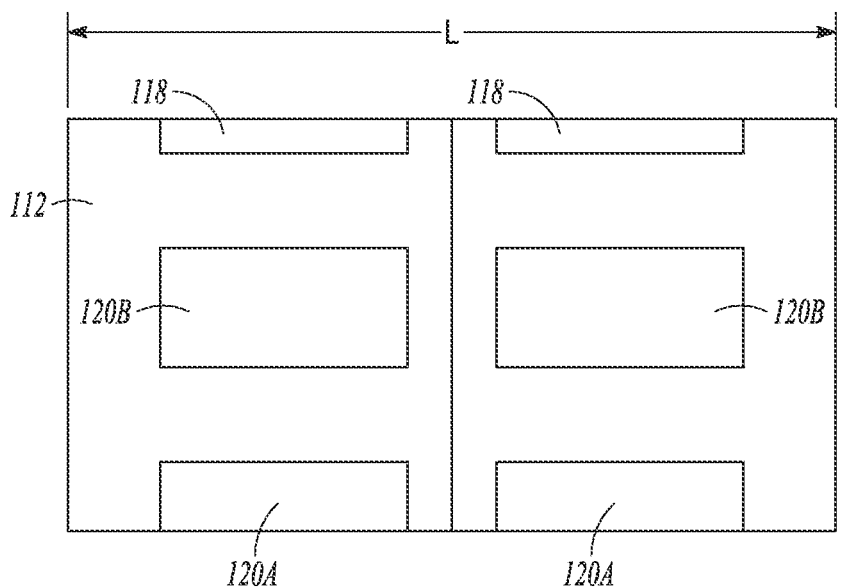
FIG. 3B is a side view of a first side of the dental regenerative device of FIG. 3.

As shown in FIG. 3, each of the first 112 and second 114 side sections can include windows or openings 120, which are shown in FIG. 3B and described in further detail below.

FIG. 3A shows an end of the dental regenerative device 100, including the first 112 and second 114 side sections, and the top section 116. The first side section 112 can include a top edge 113 and a bottom edge 115, while the second side section 114 can include a top edge 117 and a bottom edge 119. As shown in FIG. 3A, the first 112 and second 114 side sections can extend outward relative to the top section 116, in a non-parallel relationship, such that a distance D1 between the top edges 113 and 117 of the first 112 and second 114 side sections, respectively, can be less than a distance D2 between the bottom edges 115 and 119 of the first 112 and second 114 side sections, respectively. In an example, the first 112 and second 114 side sections can extend inward relative to the top section 116, in a non-parallel relationship, such that the first distance D1 can be greater than the second distance D2. In an example, the first 112 and second 114 side sections can be essentially parallel, such that the first distance D1 is substantially equivalent to the second distance D2.

The dental regenerative device 100 can be available in a variety of sizes, as well as shapes (described below), based on patient anatomy, including, for example, the patient's jaw line and the number of teeth that have been removed in an area of the mouth 10 intended to receive the dental regenerative device 100. The dental regenerative device 100 can include an overall height H and a thickness T, both of which can vary. The range of values of the height H can be based, at least in part, on an average height of the alveolar ridge 17 in humans.

The thickness T of the dental regenerative device 100 can be thick enough that the device 100 has structural integrity and thin enough to use a minimal amount of material and/or permit the device to bend or flex by at least a minimal amount. In an example, the thickness T of the dental regenerative device can be from about 0.01 inches (about 0.25 millimeters) to about 0.2 inches (about 5.1 millimeters). In another example, the thickness T can be from about 0.02 inches (about 0.51 millimeters) to about 0.08 inches (about 2.0 millimeters). In another example, the thickness T can be about 0.025 inches (about 0.64 millimeters). In another example, the thickness T can be about 0.05 inches (about 1.27 millimeters). The thickness T of the first 112 and second 114 side sections and the top section 116 can be substantially equivalent. In an example, a thickness of the top section 116 can be different than a thickness of at least one of the first 112 and second 114 side sections. In an example, a thickness can vary within each section; for example, the first side section 112 can be thinner near the top edge 113 as compared to the bottom edge 115.

FIG. 3B is a side view of the first side section 112. The first 112 and second 114 side sections can be generally identical in configuration. In an example, the first 112 and second 114 side sections can have different configurations, such as, for example, a different number or location of the openings 120. The dental regenerative device 100 can include an overall length L, and as described above, the dental regenerative device 100 can be available in different sizes having different lengths L. In an example, the dental regenerative device 100 can be generally linear along the overall length L. The dental regenerative device 100 can also have a curvature along the overall length L.

FIG. 3B shows four openings 120 in the first side section 112, as well as a portion of the openings 118 located primarily in the top section 116 and described above. Similar to the openings 118 in the top section 116, the openings 120 in the first 112 and second 114 side sections can be used to minimize the overall weight and material of the dental regenerative device 100. Alternatively or additionally, the openings 120 can be configured for securing or fixing the dental regenerative device 100 to the alveolar ridge 17, as described below.

Two openings or apertures 120 can be located generally at a bottom portion of the first side section 112 and are labeled as openings 120A. The openings 120A can be used to minimize an overall amount of material used to form the dental regenerative device 100. Two openings or apertures 120 can be located generally in a mid-section of the first side section 112 and are labeled as openings 120B. The openings or apertures 120B can be used to minimize the overall amount of material of the device 100 and/or to aid in securing the device 100 inside the mouth.

The dental regenerative device 100 can be secured to the alveolar ridge 17 using known methods and fasteners for fixing a dental implant inside the mouth 10. Such fasteners can include, for example, tacks and screws, including bone screws and bone pins. In an example, bone screws, which are commonly made of titanium or an alloy thereof, can be used to fix either or both of the first 112 and second 114 side sections to the alveolar ridge 17. In an example, the two openings or apertures 120B can be configured to receive two fasteners for securing the first side 112 to the alveolar ridge 17. Similarly, two openings 120 on the second side section 114 can be configured to receive two fasteners for securing the second side 114 to the alveolar ridge 17. Depending on a size of the openings 120B and a size of the fasteners, in an example, each of openings 120B can be configured to receive more than one fastener, such as, for example, a fastener in each end of each opening 120B.

The number of the openings or apertures 120B and the number of fasteners used to secure the dental regenerative device 100 can vary, and can depend, at least in part, on an overall size of the device 100 and where in the mouth 10 the device 100 is being implanted. The number of fasteners used can be based, at least in part, on ensuring that the device 100 is stable inside the mouth 10 once it is implanted and that the device 100 is restricted beyond minimal movement.

As shown in FIG. 3B, the openings 120B, as well as the openings 120A, can be generally rectangular in shape. In an example, the openings 120A and/or the openings 120B can have different shapes, such as, for example, a square or circular shape.

The openings 118 and 120 can be preformed in the top section 116 and the first 112 and second 114 side sections, respectively. In an example, the openings 118 and 120 can be formed (for example, drilled out) after the dental regenerative device 100 is made and prior to, or during, surgery to implant the dental regenerative device 100. Whether any or all of the openings 118 and 120 are preformed can depend on a size of the openings 118 and 120. It can be advantageous to form larger-sized openings when the dental regenerative device 100 is made to avoid having to later remove, for example, by drilling, a significant amount of material to form larger-sized openings. In some cases, it can be desirable to limit any alterations to the dental regenerative device 100 once the surgery has been started, especially once the device 100 has been placed in the mouth. As such, it can be desirable to determine a location of the openings 118 and 120 prior to implantation of the dental regenerative device 100.

Figure 4:
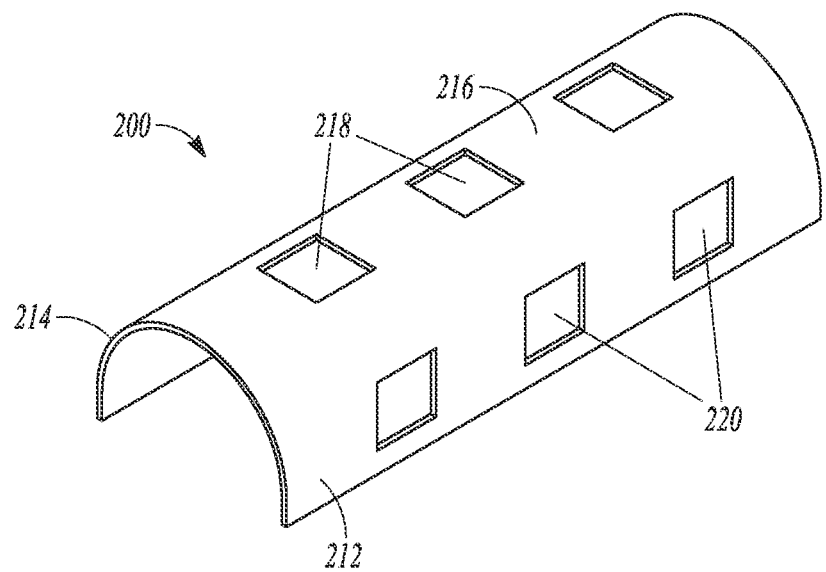
FIGS. 4-9 are perspective views of examples of dental regenerative devices in accordance with the present application.

The dental regenerative device 100 shown in FIGS. 3, 3A and 3B can be structured as an elongated arch. However, numerous other shapes and sizes for the dental regenerative devices in accordance with the present patent application are also possible. FIG. 4 shows an example of a dental regenerative device 200, which similar to the dental regenerative device 100, can include a first side section 212, a second side section 214, and a top section 216. The first 212 and second 214 side sections and the top section 216 can be a continuous piece that can form an elongated arch. As compared to dental regenerative device 100, the first 212 and second 214 side sections of the dental regenerative device 200 can have a more round or circular shape.

The top section 216 can include openings 218 which can be configured for receiving implants as described above. As shown in FIG. 4, the openings 218 can be generally rectangular in shape. Three openings 218 can be included in the top section 216, such that the dental regenerative device 200 can receive three implants. More or less openings 218 can be included in an example of the dental regenerative device 200.

The first 212 and second 214 side sections can include openings 220. As described above in reference to the dental regenerative device 100, the openings 200 can be configured for receiving a fastener or other fixation device to secure the device 200 inside the mouth. Similar to the openings 218, the openings 220 can be generally rectangular in shape. More or less openings 220 can be included in an example of the dental regenerative device 200.

Figure 5:
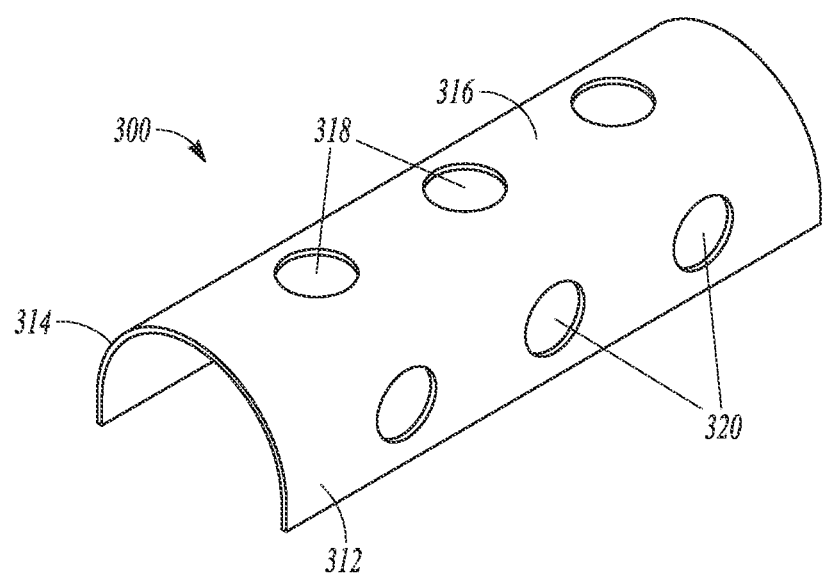

FIG. 5 shows an example of a dental regenerative device 300, which can include a first side section 312, a second side section 314, and a top section 316. Similar to the dental regenerative device 200, the dental regenerative device 300 can have a generally circular or semi-circular shape. The top section 316 can include openings 318 that can be generally circular in shape. Similarly, openings 320 can be generally circular or semi-circular in shape.

Figure 6:
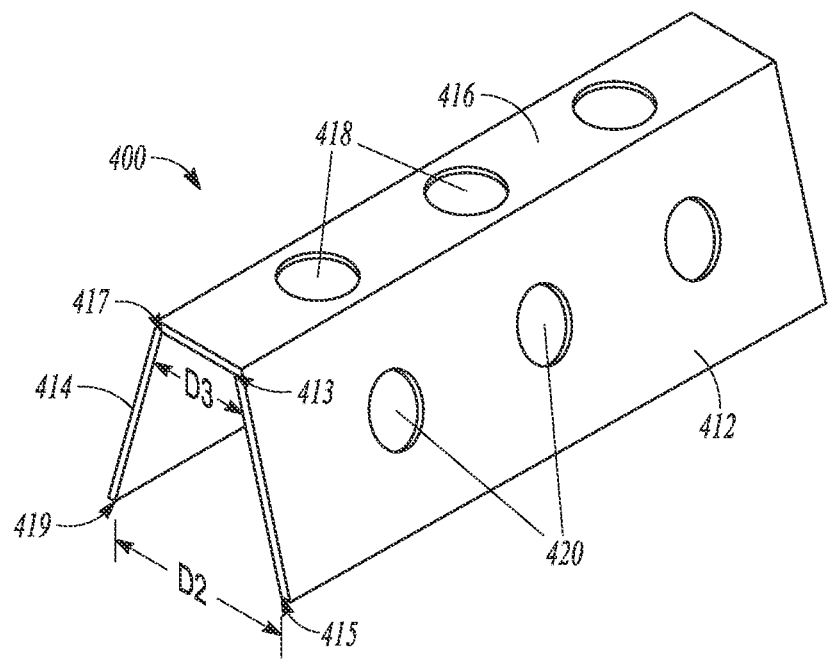

FIG. 6 shows an example of a dental regenerative device 400, which can include a first side section 412, a second side section 414, and a top section 416. The top section 416 can be generally flat or planar such that the top section 416 forms a shelf-like surface between the first 412 and second 414 side sections. The first side section 412 can include a top edge 413 and a bottom edge 415. The second side section 414 can include a top edge 417 and a bottom edge 419. A distance D3 between the top edges 413 and 417 of the first 412 and second 414 side sections, respectively, can be less than a distance D4 between the bottom edges 415 and 419 of the first 412 and second 414 side sections, respectively, such that the dental regenerative device 400 can have a generally pyramid shape. Comparing FIG. 6 to FIG. 3A, a difference between the distances D3 and D4 of the dental regenerative device 400 can be more pronounced or greater than a difference between the distances D1 and D2 of the dental regenerative device 100. The top section 416 can include three generally circular openings 418. The first 412 and second 414 side sections can include three generally circular openings 420.

Figure 7:
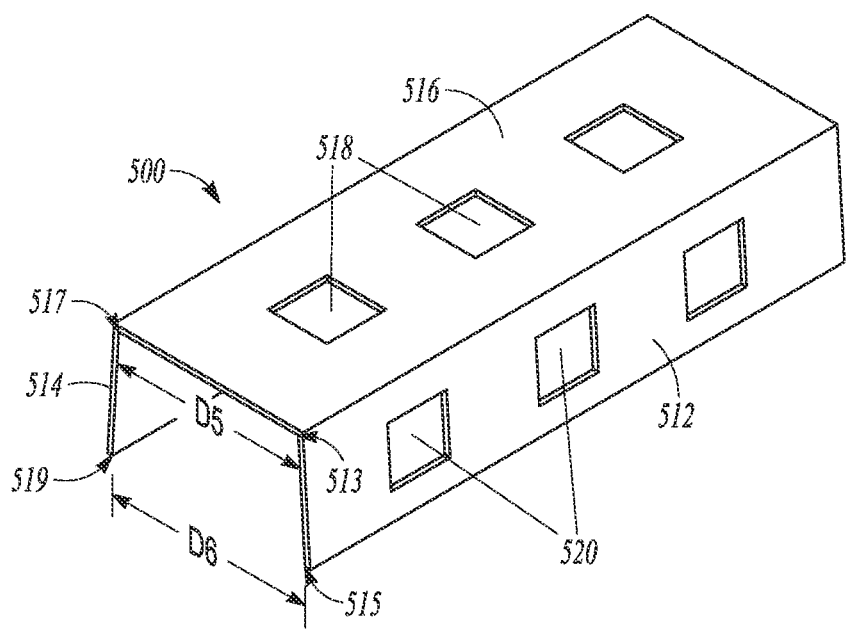

FIG. 7 shows an example of a dental regenerative device 500, which can include a first side section 512, a second side section 514, and a top section 516. The top section 516 can be generally flat or planar, similar to the dental regenerative device 400 of FIG. 6. The first side section 512 can include a top edge 513 and a bottom edge 515. The second side section 514 can include a top edge 517 and a bottom edge 519. The first 512 and second 514 side sections can be essentially parallel to one another; as such, a distance D5 between the top edges 513 and 517 of the first 512 and second 514 side sections, respectively, can be generally equal to a distance D6 between the bottom edges 515 and 519 of the first 512 and second 514 side sections, respectively. As shown in FIG. 7, the dental regenerative device 500 can have a generally rectangular shape. The top section 516 can include three openings 518, generally rectangular in shape. The first 512 and second 514 side sections can include three openings 520, generally rectangular in shape.

Various configurations of the dental regenerative device are described above and shown in FIGS. 3-7. The dental regenerative device of the present application can include any combination of the various features described above in any of the example dental regenerative devices, including an overall size, overall shape, number of openings, size of openings, and shape of openings. For example, the dental regenerative device 200 of FIG. 4 can have generally circular openings instead of the rectangular openings shown in FIG. 4 on the top section 216 and/or the first 212 and second 214 side sections. Moreover, the dental regenerative device 200 can have a longer overall length or a shorter overall length to receive more or less implants.

In examples described herein, the first and second side sections of the dental regenerative device can be generally identical in size and configuration. The first and second side sections can be different; for example, a dental regenerative device can have a first side section with more openings and/or larger openings, as compared to the second side section.

Figure 8:
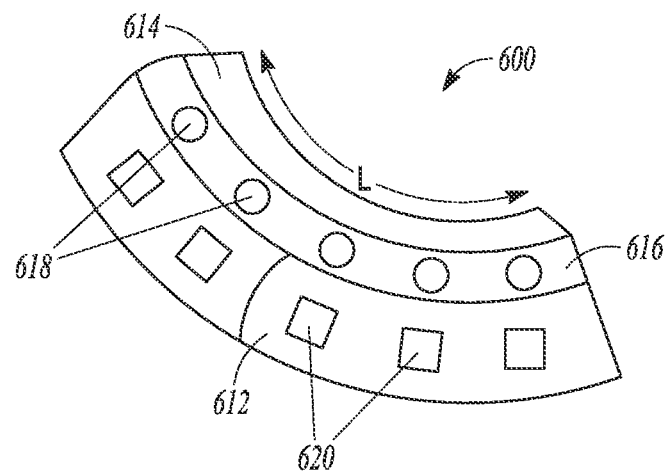

In the examples described above and shown in FIGS. 3-7, the dental regenerative device can be generally straight or linear relative to an overall length of the device. FIG. 8 shows an example of a dental regenerative device 600 that can have a curve or a bend such that the dental regenerative device forms a shape configured to conform with a non-linear shape of the maxilla or the mandible of the patient. The dental regenerative device 600 can have a greater overall length L, as compared to, for example, the dental regenerative devices 100 and 200, such that the dental regenerative device 600 can be used in an area of the mouth, for example, where more than 2, 3 or even four teeth can be removed. Because the jaw line of both the maxilla and the mandible has a generally circular or semi-circular shape, a non-linear design of the dental regenerative device 600 can conform to such shape of the jaw line. The dental regenerative device 600 can include a curvature or an arc along at least a portion of its overall length L such that the dental regenerative device 600 can be configured to conform with a shape of the maxilla or the mandible of the patient. The dental regenerative device 600 can include a first 612 and a second 614 side section, and a top section 616. Each of the first 612 and second 614 side sections and the top section 616 can include openings 620 and 618, respectively. As similarly described above, a size and a shape of the openings 618 and 620 can vary.

Figure 9:
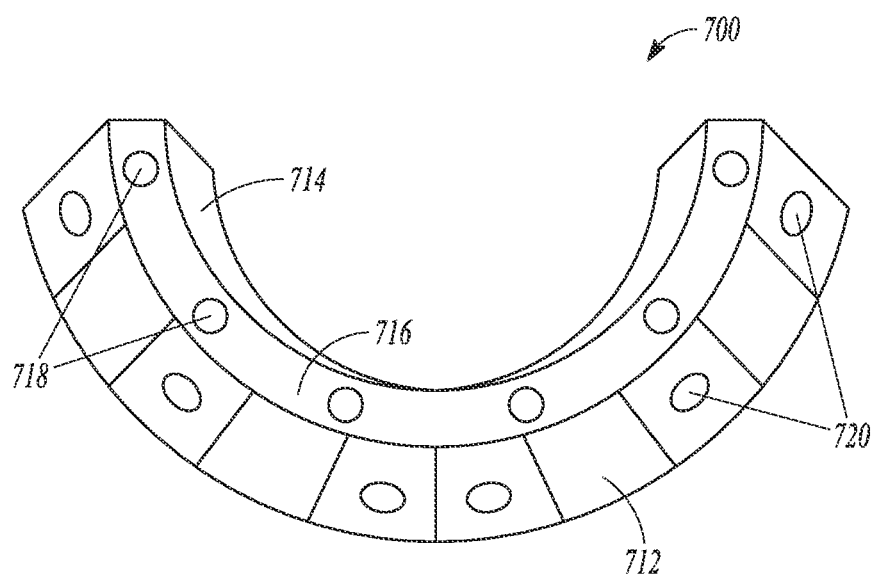

FIG. 9 shows an example of a dental regenerative device 700 that can also include an arc or curvature along an overall length of the device 700, such that the device 700 can have a generally semi-circular shape. Similar to the dental regenerative device 600, the dental regenerative device 700 can be used when several teeth have been removed. In an example, the dental regenerative device 700 can be used when all or nearly all of the teeth have been removed from the mandible or maxilla of a patient. The dental regenerative device 700 can include a first 712 and a second 714 side section, and a top section 716. Each of the first 712 and second 714 side sections and the top section 716 can include openings 720 and 718, respectively, which can vary in size and shape.

As described above, the dental regenerative device 100 (see FIG. 3) can be formed of a porous structure, such as, for example, a porous tantalum structure. Any or all of the dental regenerative devices 200, 300, 400, 500, 600 and 700, as well as the dental regenerative devices 800, 900, 1000, 1100, and 1200 described below, can also be formed of a porous structure described above.

Figure 10:
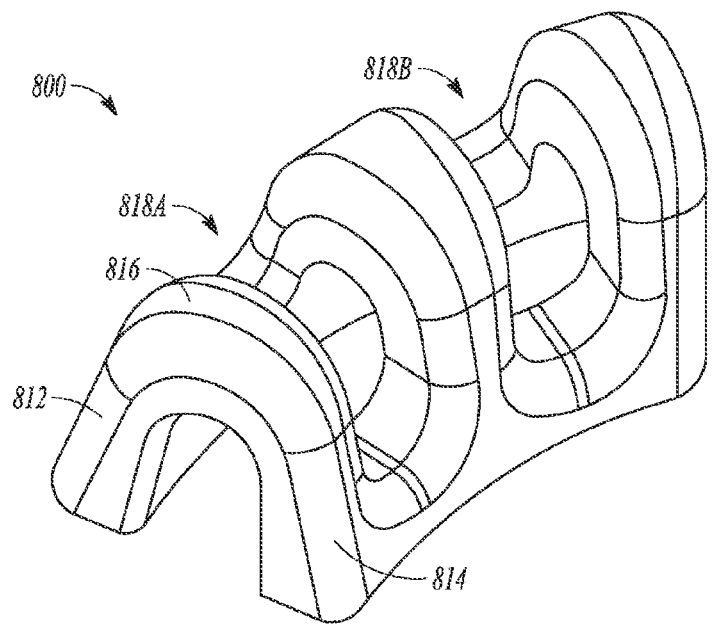
FIG. 10 is a perspective view of an example of a dental regenerative device in accordance with the present application.

FIG. 10 shows an example of a dental regenerative device 800 that can include a first side section 812, a second side section 814, and a top section 816 disposed between the first side section 812 and the second side section 814. The top section 816 can include a first opening 818A and a second opening 818B, each configured to receive an implant.

The openings 818A and 818B, as shown in FIG. 10, can extend into the first 812 and second 814 side sections. In the example shown in FIG. 10, the openings 818A and 818B can be large enough such that there is a small amount of material in the first 812 and second 814 side sections between each opening. In an example, the dental regenerative device 800 can include less surface area as compared to some of the dental regenerative devices described above having a similar overall length, such as for example, the devices 200 and 300 of FIGS. 4 and 5, respectively.

As similarly described herein for other examples of dental regenerative devices, the device 800 can be formed of a porous structure, such as a porous tantalum. As such, the device 800 can be osteoconductive and can provide structural integrity, but can also be left inside the mouth of the patient. The openings 818A and 818B can preserve an x-ray window and thus can facilitate full view, in an x-ray field, of one or more later-placed implants.

The dental regenerative device 800 is shown having two openings 818A and 818B. As similarly described above for other examples of dental regenerative devices, more or less than two openings can be included in a device having a general design similar to the device 800. The number of openings can be based, at least in part, on a number of implants to be used with the device. In an example, the device 800 having two openings 818A and 818B can be configured for use with two implants—each implant corresponding to each opening. In another example, more than one implant can be received within each opening 818A or 818B.

An overall shape of the device 800, including the top section 816 having an arched shape, can facilitate use of the device 800 as a support structure for a membrane, and in an example, the device 800 can prevent occlusal forces from compacting particulate bone graft that can be placed under the device 800.

Figure 10A:
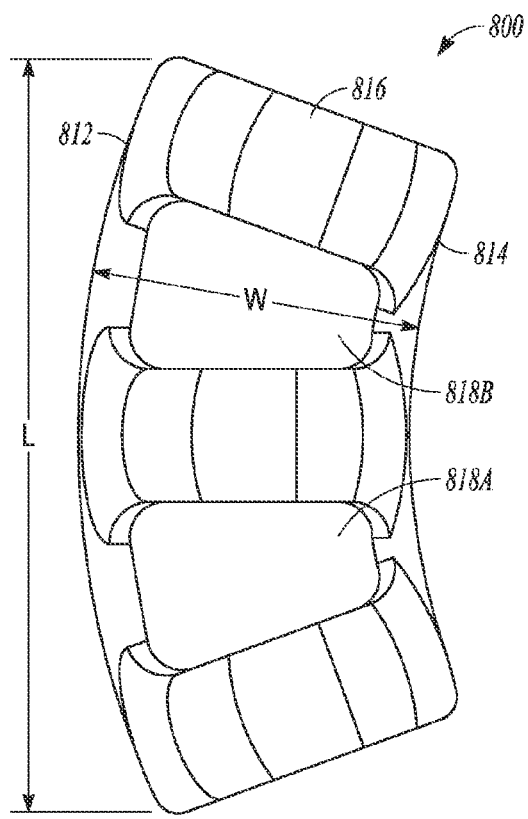
FIG. 10A is a top view of the dental regenerative device of FIG. 10.
Figure 10B:
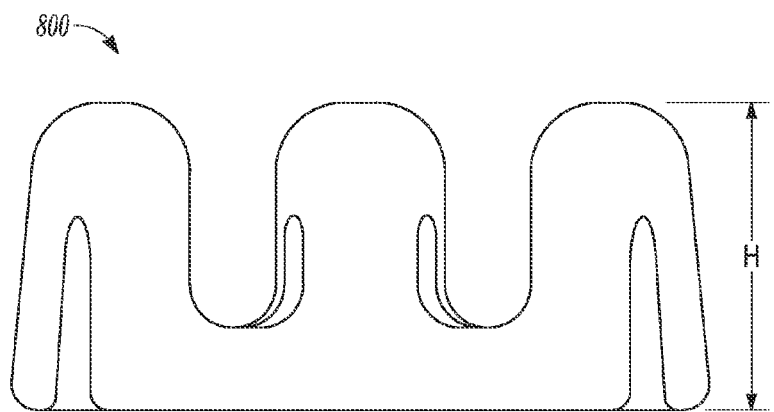
FIG. 10B is a side view of the dental regenerative device of FIG. 10.

FIG. 10A is a top view of the device 800 of FIG. 10 and illustrates that, in an example, the device 800 can have a curvature along at least a portion of an overall length L of the device 800. In an example, the overall length L can range between about 25 mm and about 50 mm; in other examples, the length L can be more or less than the provided range. The overall length can depend, in part, on a number of openings 818 formed in the device 800. FIG. 10A also shows an overall width W of the device 800. In an example, the overall width W can range between about 10 and about 20 mm; in other examples, the width W can be more or less than the provided range. FIG. 10B is a side view of the device 800 and illustrates that, in an example, the device 800 can have a generally equal height H across the overall length L of the device 800. As described in other examples below, a height of the device 800 can be variable. In an example, the height H can range between about 10 and about 20 mm; in other examples, the height H can be more or less than the provided range. Although not shown in FIGS. 10, 10A and 10B, the device 800 can include a pre-formed opening or aperture configured to receive a fastener.

Figure 11:
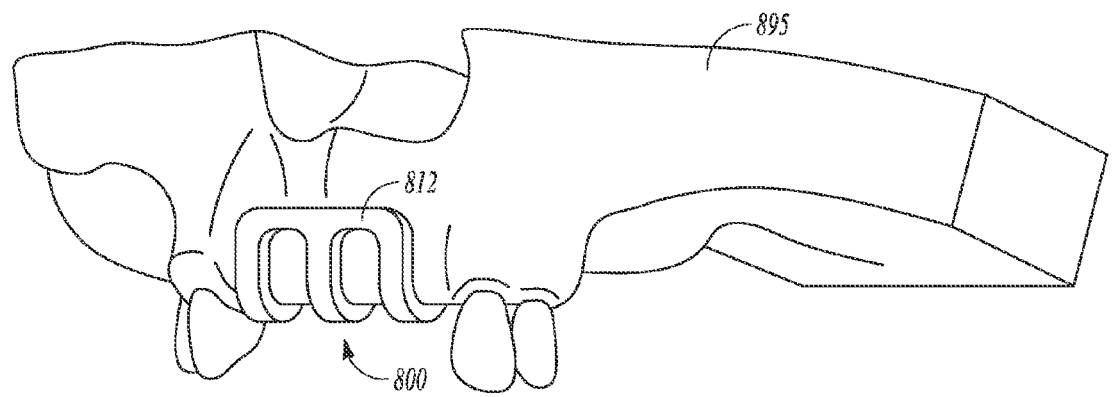
FIG. 11 is a perspective view of a skull model and the dental regenerative device of FIG. 10 placed on a maxilla of the skull model.

FIG. 11 shows the dental regenerative device 800 on a skull model 895 to illustrate an example of the device 800 for use in the mouth of a patient. As shown in FIG. 11, the device 800, having an overall curvature, can be placed on an anterior side of the maxilla of the patient. In an example, the first side 812 of the device 800 can be secured to a side of the mouth corresponding to a mesial side of the teeth. The size and the shape of the device 800 can be geometrically tailored for one or more areas of the mouth. The device 800 can also be used for the mandible of the mouth. In the example of FIG. 11, the device 800 can be configured for use with two implants.

Figure 12:
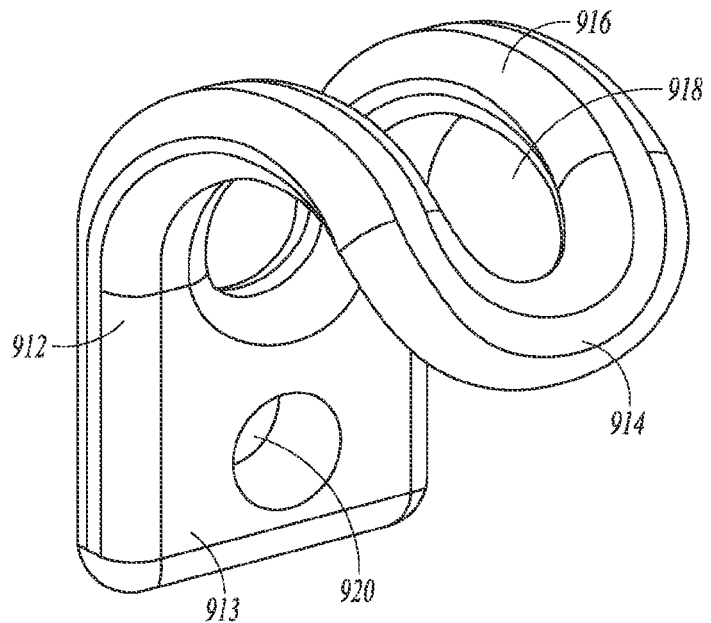
FIG. 12 is a perspective view of an example of a dental regenerative device in accordance with the present application.
Figure 12A:
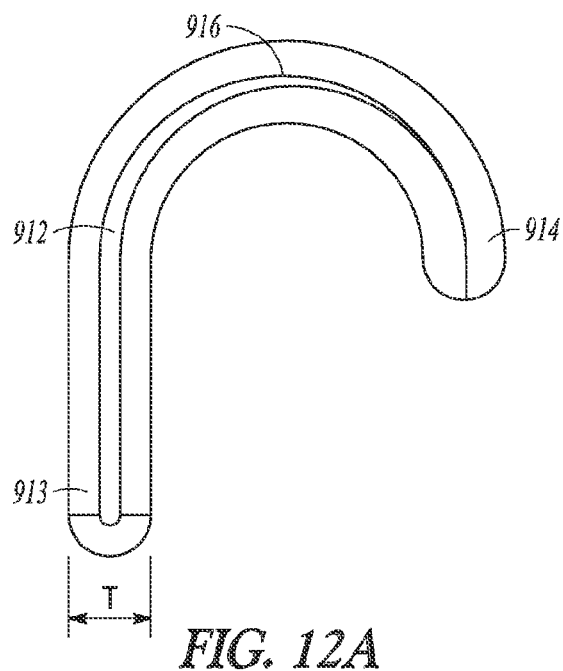
FIG. 12A is a side view of the dental regenerative device of FIG. 12.
Figure 12B:
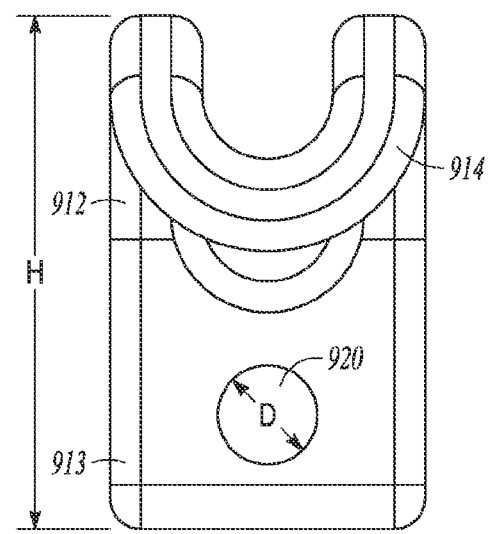
FIG. 12B is a back view of the dental regenerative device of FIG. 12.

FIG. 12 shows an example of a dental regenerative device 900 that can include a first side section 912, a second side section 914, and a top section 916 disposed between the first 912 and second 914 side sections. FIG. 12A shows a side view of the dental regenerative device 900 and FIG. 12B shows a back view of the device 900. The top section 916 can include an opening 918 that can also extend into the first 912 and second 914 side sections, and can be configured to receive an implant. The first side section 912 can extend past an end of the second side section 914 and can include an attachment portion 913. The attachment portion 913 can include at least one aperture 920 configured for receiving a fastener for attachment of the device 900 in the mouth. FIGS. 12 and 12B do not necessarily show the aperture 920 to scale with an overall size of the device 900; in an example, the aperture 920 can be smaller than it is shown in FIG. 12. In an example, a diameter D of the aperture 920 can be between about 1 and about 2.5 mm; in other examples, the diameter D can be more or less than the provided range. The device 900 can have an overall thickness T such that the device 900 has structural integrity while minimizing overall material, in part to permit at least some bend or flex of the device 900. In an example, the thickness T of the device 900 can be between about 0.5 and about 2 mm; in other examples, the thickness T can be more or less than the provided range. In an example, an overall height H of the device 900 can be between about 10 and about 25 mm; in other examples, the height H can be more or less than the provided range. In other examples, the device 900 can include more than the one opening 918 shown in FIG. 12.

Figure 13:
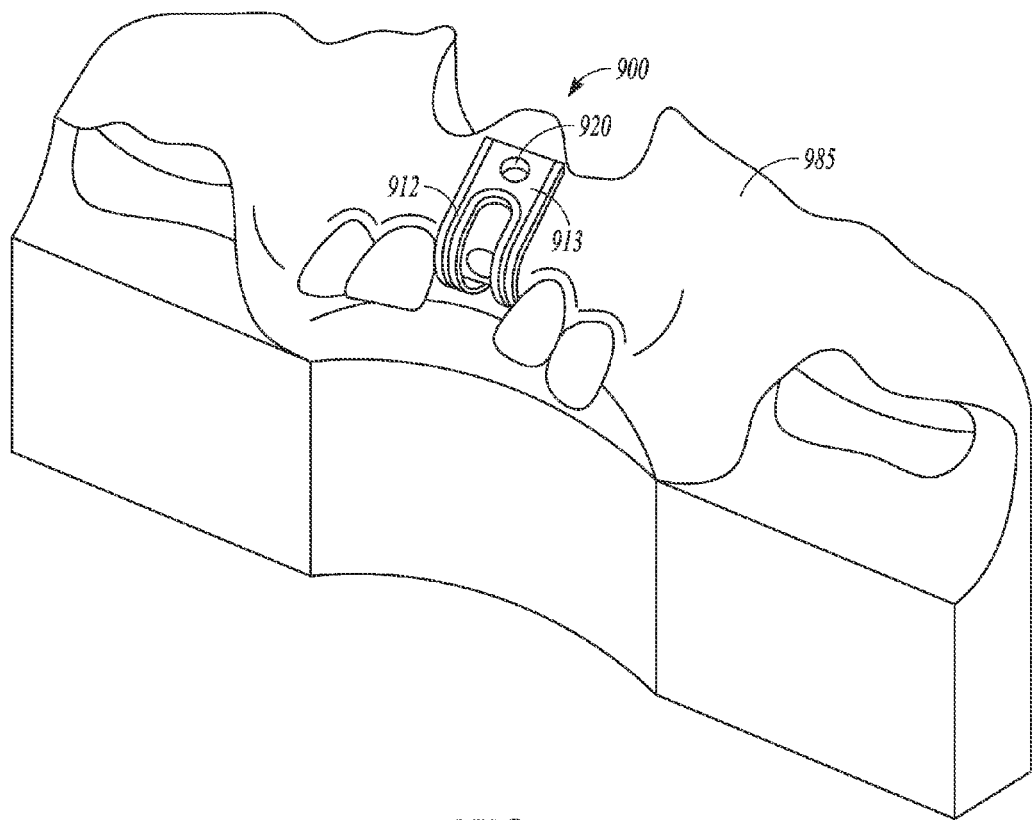
FIG. 13 is a perspective view of a skull model and the dental regenerative device of FIG. 12 placed on a maxilla of the skull model.

FIG. 13 shows the dental regenerative device 900 on a skull model 995. The first side 912 of the device 900, including the attachment portion 913, can be placed on a mesial side of the maxilla of the mouth. The second side 914 of the device 900 can be placed on the distal side of the mouth. After the device 900 is properly placed, a fastener can be inserted into the bone through aperture 920. The device 800, as shown in FIG. 11, can be configured for use with two implants, whereas the device 900, as shown in FIG. 13, can be configured for use with one implant. In other examples, a device including an attachment portion, similar to the device 900, can have two or more openings for receiving two or more implants.

Figure 14:
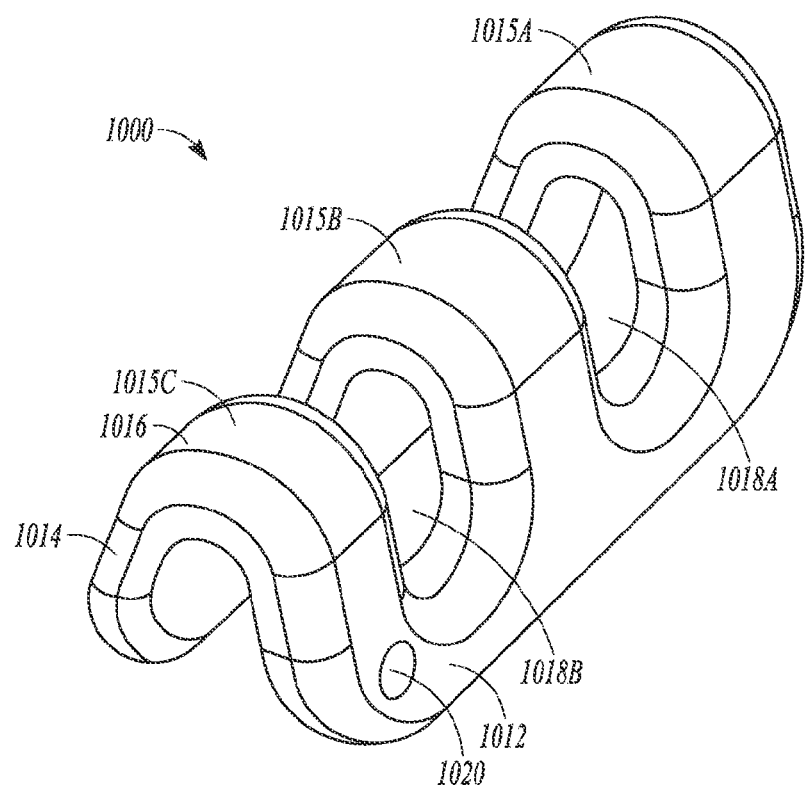
FIG. 14 is a perspective view of an example of a dental regenerative device in accordance with the present application.
Figure 14A:
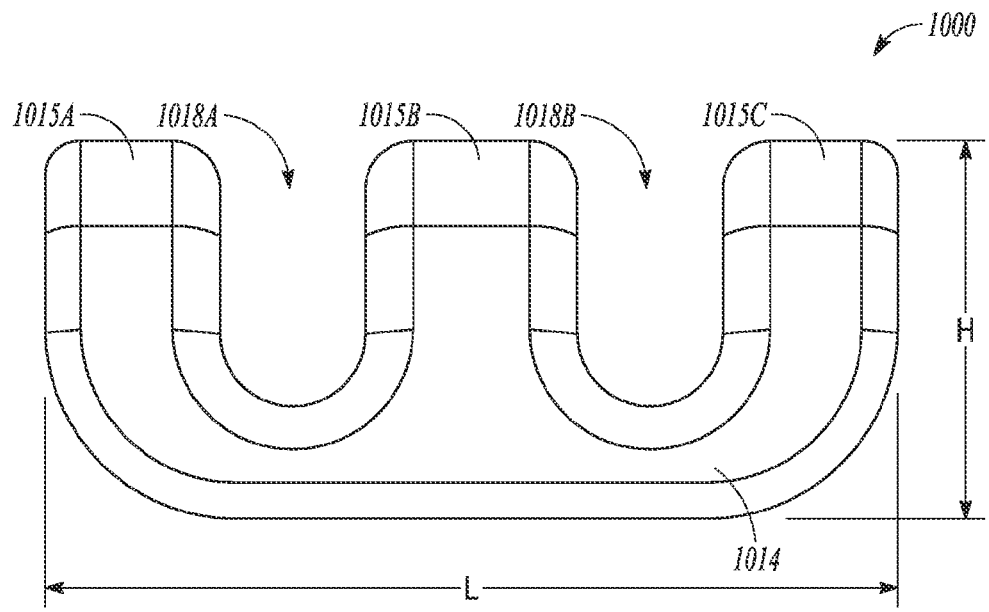
FIG. 14A is a side view of the dental regenerative device of FIG. 14.

FIGS. 14 and 14A show an example of a dental regenerative device 1000 that can be similar to the device 800 of FIG. 10. The dental regenerative device 1000 can include a first side section 1012, a second side section 1014, and a top section 1016 disposed between the first 1012 and second 1014 side sections. The device 1000 can include openings 1018A and 1018B, which can be formed in the top section 1016 and extend into the first 1012 and second 1014 side sections. The dental regenerative device 800 (FIG. 10) is shown having a curvature along at least a portion of its length, whereas the dental regenerative 1000 can be generally linear along an overall length L of the device 1000. In an example, the length L of the device 1000 can range between about 25 mm and about 50 mm; in other examples the length L can be more or less than the provided range. The length L can also vary depending, in part, on a number of openings 1018.

The dental regenerative device 1000 can include an aperture 1020 for receiving a fastener. In other examples, the dental regenerative device 1000 can include one or more apertures similar to aperture 1020 on the first side section 1012 and/or the second side section 1014. FIG. 14A shows the second side section 1014, which in an example, does not include an aperture like the aperture 1020 on the first side section 1012.

As shown in FIG. 14A, the device 1000 can have a generally equal height H across the length L of the device 1000. In other examples, the height H of the device 1000 can be variable. In an example, the height H can range between about 10 and about 20 mm; in other examples, the height H can be more or less than the provided range. The top section 1016 of the device 1000 can have an overall curved shape and the top section 1016 can include arch segments 1015A, 1015B and 1015C. Openings 1018A and 1018B can be defined between each pair of adjacent arch segments 1015. The design of the device 1000 including the arch segments 1015 can facilitate use of the device 1000 in supporting a membrane and preventing or minimizing particulate bone compact due to occlusal forces.

Figure 15:
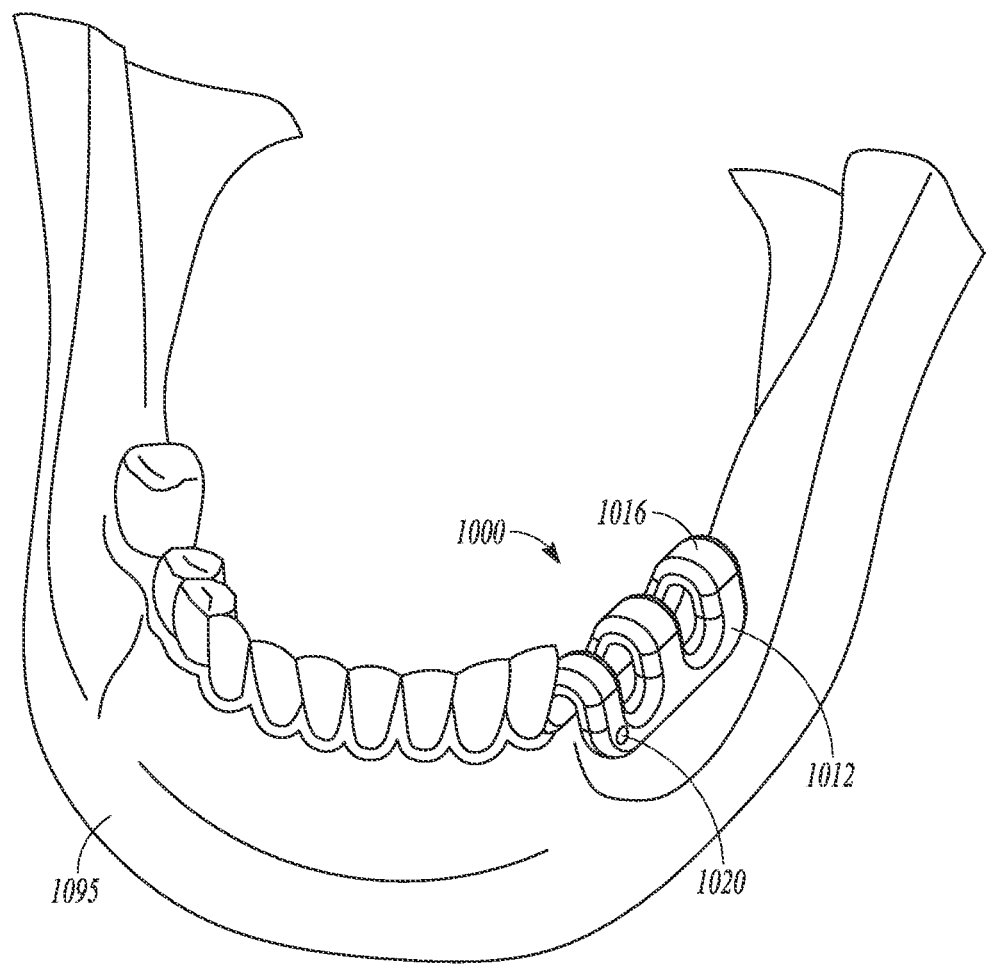
FIG. 15 is a perspective view of a skull model and the dental regenerative device of FIG. 14 placed on a mandible of the skull model.

FIG. 15 shows the dental regenerative device 1000 on a skull model 1095. As shown, the device 1000 can be attached to a posterior region of the mandible. As described above, the dental regenerative devices can be tailored to a particular area of the mouth. Because the device 1000 is generally straight or linear from end to end, in an example, the device 1000 can be used in a more posterior region, either on the mandible or the maxilla of the mouth. The first side section 1012 can be attached to an outside of the mandible and a fastener can be inserted through the aperture 1020 to secure the device 1000.

Figure 16:
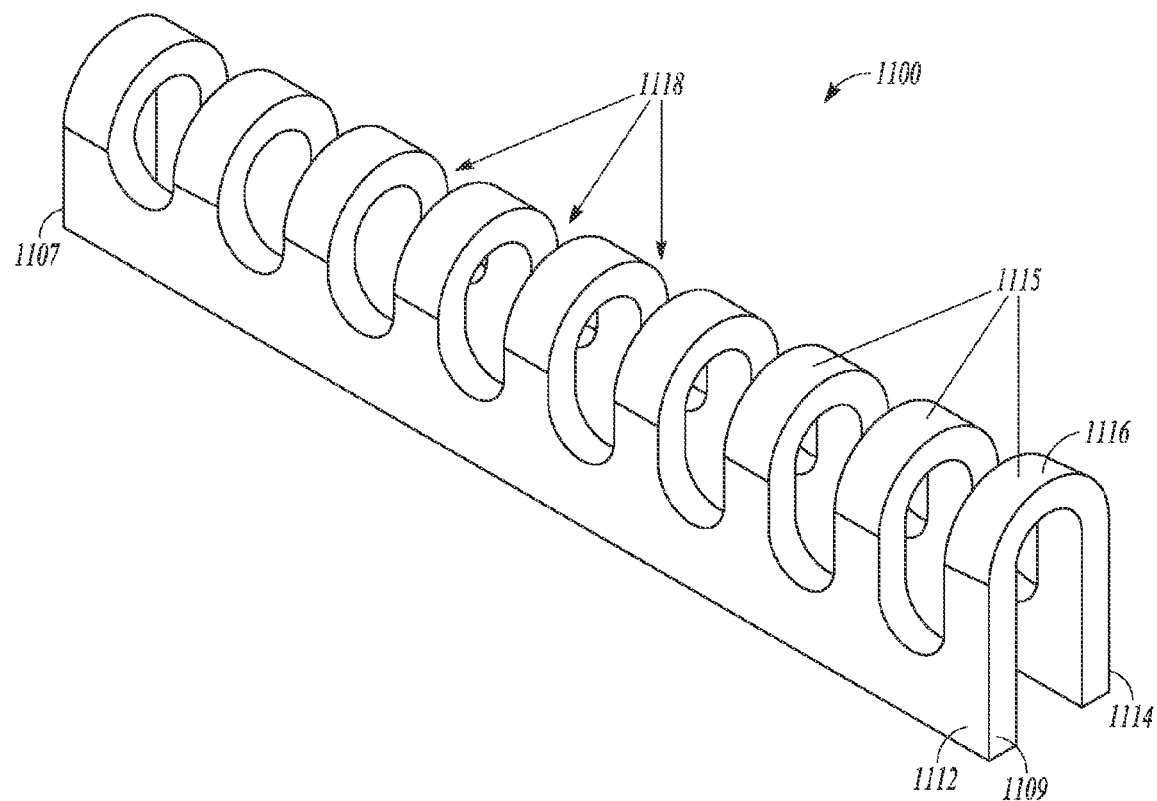
FIG. 16 is a perspective view of an example of a dental regenerative device in accordance with the present application.
Figure 16A:
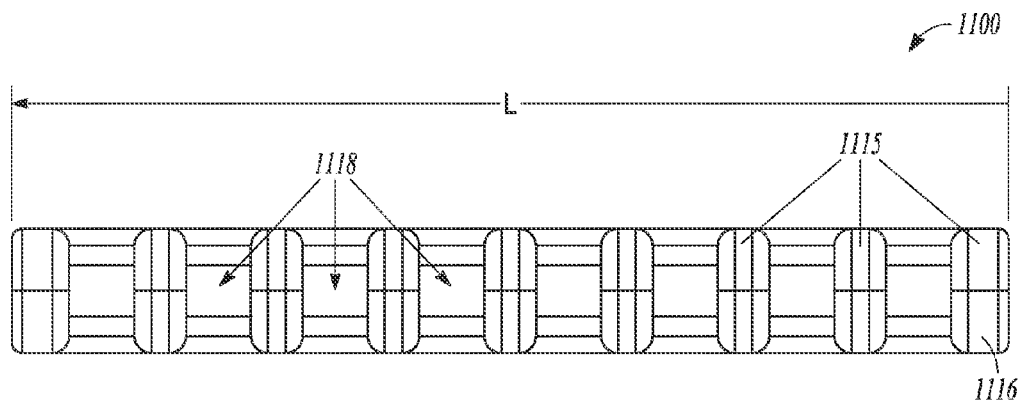
FIG. 16A is a top view of the dental regenerative device of FIG. 16.

FIG. 16 shows an example of a dental regenerative device 1100 including a first side section 1112, a second side section 1114, and a top section 1116 disposed between the first 1112 and second 1114 side sections. As similarly described above, the top section 1116 can include a plurality of arch segments 1115 and an opening 1118 can be defined between each part of adjacent arch segments 1115. In the example shown in FIG. 16, the dental regenerative device 1100 can include eight openings 1118. Although it may be unlikely that a device 1100 having an overall length L as shown in FIG. 16A (a top view of the device 1100) would be implanted in a portion of a patient's mouth, the device 1100 illustrates that the dental regenerative devices of the present application can include any number of openings and overall sizes. In an example, the length L of the device 100 can range between about 50 and about 100 mm; in other examples, the length L can be more or less than the provided range. The length L of the device can be based, in part, on the number of arch segments 1115 and openings 1118.

Figure 16B:
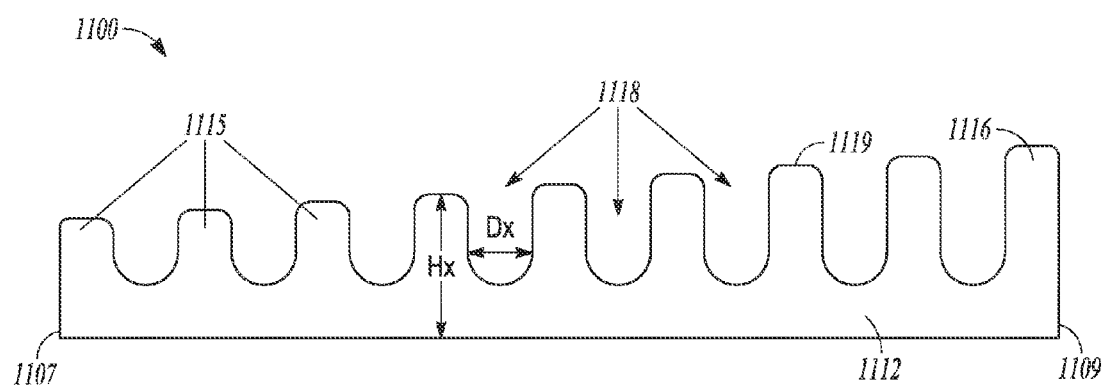
FIG. 16B is a side view of the dental regenerative device of FIG. 16.

FIG. 16B shows a side view of the first side section 1112 of the device 1100, and illustrates a difference in height between the plurality of arch segments 1115. (Each arch segment 1115 can have a height $H_X$) In an example, the arch segments 1115 can increase in height, moving from a first end 1107 to a second end 1109 of the device 1100. In such example, the height $H_X$ at or near the first end 1107 can be about 10 mm and the height $H_X$ can increase by 1-2 mm increments for each arch segment 1115. In an example, at least one of the arch segments 1115 can have a height equal to a height of another arch segment 1115. In an example, the arch segments 1115 can all have a generally equal height to one another. In an example, the height $H_X$ of each of the arch segments 1115 can range between about 10 and about 20 mm; in other examples, the height $H_X$ can be more or less than the provided range.

A distance $D_X$ between each pair of adjacent arches 1115, which correlates to a size of each of the openings 1118, can be generally equal across a length of the device 1100. In another example, the distance $D_X$ can vary across the length L of the device 1100. In an example, the distance $D_X$ between each arch segment 1115 can range between about 3.5 and about 7 mm; in other examples, the distance $D_X$ can be more or less than the provided range. An uppermost part 1119 of the top portions can be tapered or generally straight. Apertures are not shown in FIG. 16 or 16B on the first 1112 and/or second 1114 side sections, but apertures for receiving a fastener, as similarly described above, can be included on at least one of the first 1112 and/or second 1114 side sections.

Figure 17:
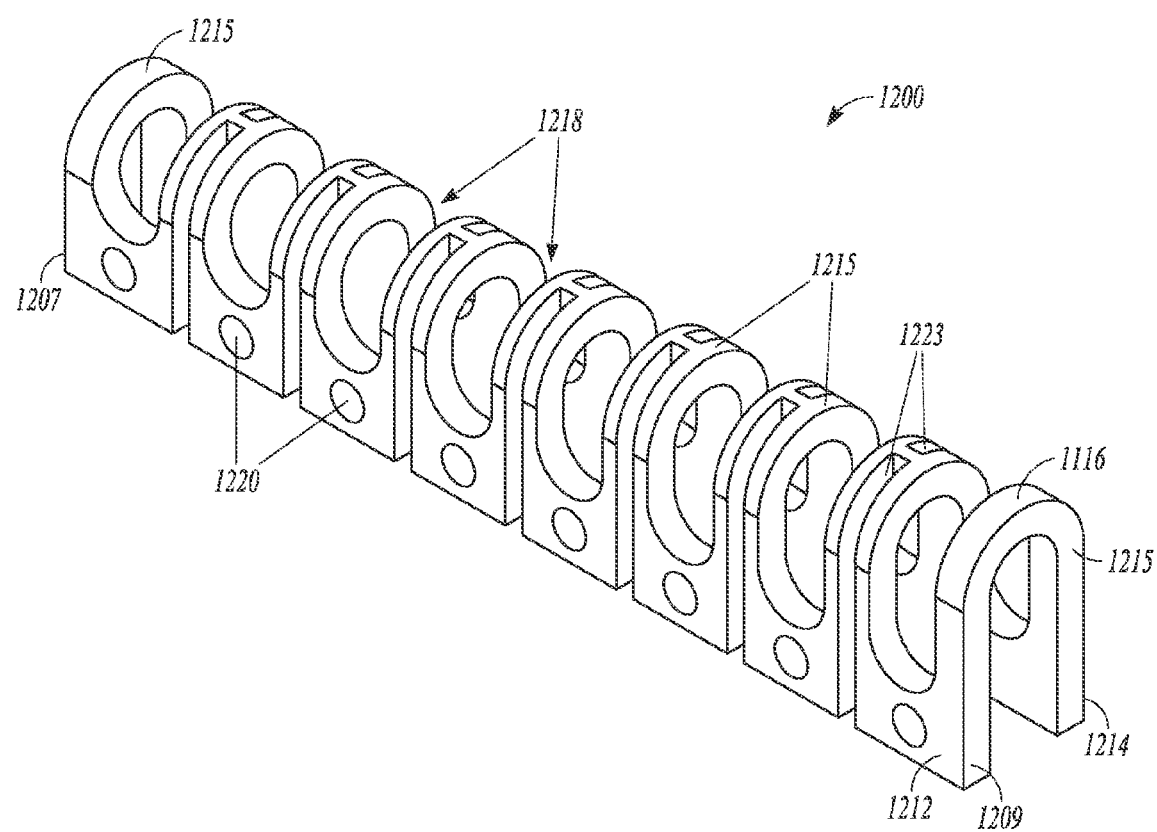
FIG. 17 is a perspective view of an example of a porous structure in accordance with the present application for use as one or more dental regenerative devices.

FIG. 17 shows an example of a porous structure 1200 that can be similar to the dental regenerative device 1100 of FIG. 16, and can include a first side section 1212, a second side section 1214, and a top section 1216 having a plurality of arch segments 1215 and a plurality of openings 1218. In an example, the porous structure 1200 can be formed of tantalum as described above. At least some of the arches 1215 can include a groove or slot 1223 formed in at least a portion of the arch segment 1215. In an example, as shown in FIG. 17, the groove 1223 can extend from the top section 1116 and into at least a portion of the first 1212 and second 1214 side sections. In an example, one or more of the arch segments 1215 at the first 1207 and second 1209 ends of the porous structure 1200 may not include the grooves 1223. In another example, all of the arches 1215 of the porous structure 1200 can include the grooves 1223. In another example, every other arch 1215 of the porous structure 1200 can include a groove 1223.

The porous structure 1200 can be configured for use as one or more ridge augmentation devices (or dental regenerative devices) that can be attached to the alveolar ridge inside a mouth of a patient. The porous structure 1200 can be longer or shorter than the example shown in FIG. 17 having nine arches 1215 and eight openings 1218. The porous structure 1200 can be configured such that segments of the porous structure 1200 can be detached from the overall structure 1200, and one or more of the segments can be used as a dental regenerative device, as described above. The grooves 1223 formed in the arches 1215 of the porous structure 1200 can be configured to create detachment points at the arches 1215 that can be cut, clipped or bent, such that segments having one or more openings 1218 can be individually created from the porous structure 1200. Other features, in addition to or as an alternative to the grooves 1223, can be incorporated into the porous structure 1200 to create detachment points.

The grooves 1223 can be created using known processes for creating a groove or slot in a metal structure. In an example, a secondary process can be used to form the grooves 1223 after the porous structure 1200 has been formed using, for example, the process described above for Trabecular Metal™ Technology. This secondary process can include, for example, electrical discharge machining (EDM) technology.

The porous structure 1200 can be used to form one or more dental regenerative devices, each of the dental regenerative device segments having at least one opening 1218. A particular length of the segment formed from the porous structure 1200 can be determined prior to or during a surgery to implant the dental regenerative device. Once the appropriate length or section of the porous structure 1200 is determined, a user can clip or cut the porous structure 1200 along the appropriate groove 1223 in the porous structure 1200. If an originally-selected segment is determined to not have a sufficient fit for placement in the mouth, the user can select one or more additional segments until the right segment is selected for the patient.

In an example, a particular segment of the porous structure 1200 can be selected based in part on a height of the arches 1215. As described above in reference to FIG. 16B, the height of the arches 1215 of the porous structure 1200 can vary and a particular segment selected from the porous structure 1200 can depend, for example, on the needs of each patient and/or the size and shape of the bone deficiency.

In an example, as shown in FIG. 17, a number of apertures 1220 in the porous structure 1200 can correspond to the number of openings 1218 in the porous structure 1200. In another example, the number of apertures 1220 can be more or less than the apertures 1220 shown in FIG. 17. If a ridge augmentation or regenerative device is formed having two or more openings 1218, a number of fasteners used to secure the device in the mouth can be less than the number of openings 1218. All of the apertures 1220 do not have to have a corresponding fastener. The user can select a number of fasteners sufficient to secure the device to the alveolar ridge.

In an example, if a portion of the porous structure 1200 is unused after an operation is complete, the remaining portion of the porous structure 1200 can be re-sterilized and used in a future operation.

Multiple examples of dental regenerative devices are shown and described herein, and each of the devices can have varying dimensions, including an overall length, width and height, based on, for example, patient needs, bone defects, and mouth size. It is recognized that not all examples are explicitly illustrated herein and other lengths and combinations of the above described features are included in the dental regenerative devices of the present application.

In an example, a patient-specific dental regenerative device can be prepared for a specific patient, prior to surgery, such as based on a size and shape of the patient's alveolar ridge in an area of the maxilla or mandible where teeth have been removed. The user can design the dental regenerative device with the number of openings, as well as the size of the openings, suited for the particular patient. As mentioned above, the user may want to minimize an amount of material used to form the dental regenerative device, while maintaining structural integrity of the device and facilitating fixation of implants and attachment mechanisms.

A set of dental regenerative devices can be provided in a kit, or as individual components, to allow the user to select a dental regenerative device from a variety of devices having different sizes, shapes, etc. In an example, a kit can include dental regenerative devices having preformed openings and dental regenerative devices that can have some or all of the openings formed intra-operatively. The kit can provide the user flexibility, if, for example, the user initially chooses a particular dental regenerative device that is not an ideal size and/or shape for a particular patient's mouth. The user can then select another dental regenerative device from the kit. In an example, the kit can be pre-packaged and can include a hermetic seal. The components inside the kit can be sterilized prior to packaging or the kit can be formed of a material capable of withstanding sterilization. In an example, the kit can include instructions for use (IFUs) for selecting a dental regenerative device for a particular application. The instructions for use can be included inside the kit or accompany the kit. As an alternative or in addition to a kit, the user can be provided or obtain multiple dental regenerative devices, which can be separately packaged or separately provided to the user, and the multiple devices can have different sizes and shapes, including some or all of the dental regenerative devices described herein. The user can select the one or more devices suited to a particular patient. Reference is made to co-pending application Ser. No. 13/838,341, entitled DENTAL IMPLANT WEDGES and filed on Mar. 15, 2013, which includes disclosure of additional shapes of dental implants.

The dental regenerative device is described herein as being used to promote vertical and/or horizontal bone growth in the mouth, such that dental implants can be loaded into the mouth. In some cases, a patient's bone loss or bone resorption can be significant enough that, even with bone regeneration or ridge augmentation, implants may not be suitable, and the patient may have to use dentures instead. The dental regenerative device described herein can be used to regenerate a sufficient amount of bone such that dentures can be better placed inside the patient's mouth.

The present disclosure includes a method of performing ridge augmentation of a maxilla or a mandible of a patient in order to regenerate bone. The method can include making an incision or cut in the tissue in an area where a dental regenerative device is intended to be implanted. The teeth typically have been previously removed from the intended area. The tissue can be pulled back, exposing the bone. Bone grafting material and/or bone filler can be used depending, at least in part, on the extent of bone resorption in the area. The method can include securing the dental regenerative device to the exposed portion of the bone. A first and/or a second side of the dental regenerative device can be attached to the alveolar ridge using known fixation devices and methods. As described above, the openings or apertures for receiving the fixation devices can be included in the dental regenerative device, as made, or the openings or apertures can be formed prior to or as part of the implantation surgery. In an example, a membrane can be placed over the regenerative device, such as to prevent soft tissue growth through the dental regenerative device before bone growth can occur. After the dental regenerative device and, if applicable, the membrane, are secured inside the mouth, the tissue around the bone can be closed. As mentioned above, the implants can be loaded during this same surgery or in a later surgery, such that the bone has time to regenerate with the aid of the dental regenerative device.

The method of performing the ridge augmentation can include selecting an appropriate size and shape of the regenerative device, prior to securing the dental regenerative device to the exposed portion of the bone. The regenerative device can be selected based in part on the area of the mouth corresponding to the exposed bone, a size of the bone defects, and a number of implants intended to be used with the dental regenerative device. In an example, the regenerative device can be detached from an elongated porous structure configured for use as one or more dental regenerative devices. One or more grooves can be formed in the porous structure to create detachment points on the porous structure.

The dental regenerative device described herein can have versatility and flexibility for use in different areas of the mouth. The dental regenerative device can include a variety of shapes and sizes, and can be used with known fixation methods and devices to secure the device inside the mouth. Because the device can be formed from a porous metal material, suitable for permanent implantation in the mouth, the device does not have to be removed from the mouth in a later surgery. Because the porous metal material can form a rigid structure, the device can be used without an accompanying support structure that may require a later surgery to remove the support structure. The porous metal material can facilitate vertical bone growth and horizontal bone growth around the area in the mouth where the device is implanted, such that the device helps in regenerating the bone in the alveolar ridge prior to and/or after the dental implants are loaded inside the mouth.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

To further illustrate the ridge augmentation or dental regenerative devices and methods disclosed herein, a non-limiting list of examples is provided here:

In Example 1, a regenerative device configured for placement on an alveolar ridge in a maxilla or a mandible of a patient can comprise a first side section, a second side section, and a top section extending between and connecting the first and second side sections. The top section and the first and second side sections can each be formed from a porous material that is configured to retain its structure after implantation in a patient. The top section can include one or more openings formed in the top section and configured for receiving an implant.

In Example 2, the regenerative device of Example 1 can optionally be configured such that the top section, the first side section, and the second side section form an elongated arch.

In Example 3, the regenerative device of Example 1 can optionally be configured such that the top section is curved such that the regenerative device has a generally semi-circular shape.

In Example 4, the regenerative device of any one or any combination of Examples 1-3 can optionally be configured such that the one or more openings extend into at least one of a portion of the first side section and a portion of the second side section.

In Example 5, the regenerative device of any one or any combination of Examples 1-4 can optionally be configured such that the regenerative device is generally linear along an overall length of the regenerative device.

In Example 6, the regenerative device of any one or any combination of Examples 1-5 can optionally be configured such that the regenerative device has a curvature along at least a portion of an overall length of the regenerative device such that the regenerative device is configured to conform with a shape of a maxilla or a mandible of the patient.

In Example 7, the regenerative device of any one or any combination of Examples 1-6 can optionally be configured such that the first side section includes a first aperture configured for receiving a first fastener to secure the device to an alveolar ridge of the patient.

In Example 8, the regenerative device of Example 7 can optionally be configured such that the second side section includes a second aperture configured for receiving a second fastener to secure the device to the alveolar ridge.

In Example 9, the regenerative device of any one or any combination of Examples 1-8 can optionally be configured such that an end of the first side section extends past an end of the second side section to form an attachment portion, and the attachment portion is configured for attachment to the alveolar ridge.

In Example 10, the regenerative device of Example 9 can optionally be configured such that the attachment portion includes at least one aperture configured for receiving a fastener.

In Example 11, the regenerative device of any one or any combination of Examples 1-10 can optionally be configured such that the regenerative device is configured for anterior placement in the maxilla or mandible of the patient.

In Example 12, the regenerative device of any one or any combination of Examples 1-11 can optionally be configured such that the top section includes at least two openings.

In Example 13, the regenerative device of any one or any combination of Examples 1-12 can optionally be configured such that the porous material is a porous tantalum structure.

In Example 14, a ridge augmentation device can comprise an elongated arch having a first side portion, a second side portion, and a top portion disposed between the first and second side portions. The elongated arch can be formed of a porous metal and can be configured to be secured to an alveolar ridge of a patient. The top portion can include one or more openings configured for receiving an implant.

In Example 15, the ridge augmentation device of Example 14 can optionally be configured such that the top portion includes two or more openings.

In Example 16, the ridge augmentation device of any one or any combination of Examples 14 or 15 can optionally be configured such that the porous metal is tantalum.

In Example 17, the ridge augmentation device of any one or any combination of Examples 14-16 can optionally be configured such that the one or more openings extend into a portion of the first side section and a portion of the second side section.

In Example 18, the ridge augmentation device of any one or any combination of Examples 14-17 can optionally be configured such that the top portion includes a plurality of arch segments, and the one or more openings are defined between each pair of adjacent arch segments.

In Example 19, the ridge augmentation device of Example 18 can optionally be configured such that at least one of the arch segments includes a groove configured to create a detachment point for a selected portion of the ridge augmentation device to be detachable from a remaining portion of the ridge augmentation device.

In Example 20, the ridge augmentation device of any one or any combination of Examples 18 or 19 can optionally be configured such that the plurality of arch segments have a generally equal height to one another.

In Example 21, the ridge augmentation device of any one or any combination of Examples 18 or 19 can optionally be configured such that at least one of the arch segments has a different height than at least one of the other arch segments.

In Example 22, a porous structure, configured for use as one or more ridge augmentation devices for placement in a maxilla or a mandible of a patient, can comprise a first side section, a second side section, and a top section extending between and connecting the first side section and the second side section. The top section can have a curved shape and can define a plurality of arch segments, wherein an opening is defined between each pair of adjacent arch segments and is configured for receiving an implant. At least one of the arch segments can include a groove configured to allow a selected portion of the porous structure to be detached for use as a ridge augmentation device.

In Example 23, the porous structure of Example 22 can optionally be configured such that the porous structure is generally linear along an overall length of the porous structure.

In Example 24, the porous structure of Example 22 can optionally be configured such that the porous structure has a curvature along at least a portion of an overall length of the porous structure.

In Example 25, the porous structure of any one or any combination of Examples 22-24 can optionally be configured such that the first side section includes a plurality of apertures, each aperture configured for receiving a fastener to attach the porous structure or a portion thereof to an alveolar ridge of a patient.

In Example 26, the porous structure of any one or any combination of Examples 22-25 can optionally be configured such that the plurality of arch segments have a generally equal height to one another.

In Example 27, the porous structure of any one or any combination of Examples 22-25 can optionally be configured such that at least one of the arch segments has a different height than at least one of the other arch segments.

In Example 28, the porous structure of any one or any combination of Examples 22-27 can optionally be configured such that the porous structure is tantalum.

In Example 29, a method of performing ridge augmentation of a maxilla or a mandible of a patent to regenerate bone can include exposing a portion of the bone that forms the alveolar ridge in the maxilla or the mandible of the patient by cutting through tissue covering the bone and securing a regenerative device to the exposed portion of the bone. The regenerative device can include an opening configured for receiving an implant and formed of a porous metal that retains its structure after implantation in the maxilla or the mandible. The method can include closing the tissue around the exposed portion of the bone and the regenerative device.

In Example 30, the method of Example 29 can optionally further comprise placing a membrane over the regenerative device, prior to closing the surrounding tissue around the exposed portion of the bone and the regenerative device, wherein the membrane is formed of a material that prevents soft tissue from growing into the porous metal of the regenerative device.

In Example 31, the method of any one or any combination of Examples 29 or 30 can optionally further comprise placing bone graft in and around the exposed bone, prior to securing the regenerative device to the bone.

In Example 32, the method of any one or any combination of Examples 29-31 can optionally be configured such that securing the regenerative device to the exposed portion of the bone includes attaching a first side portion of the regenerative device to an alveolar ridge of the patient using at least one fastener.

In Example 33, the method of any one or any combination of Examples 29-32 can optionally further comprise selecting an appropriate size and shape of the regenerative device, prior to securing the regenerative device to the bone.

In Example 34, the method of Example 33 can optionally be configured such that selecting an appropriate size and shape of the regenerative device includes separating the regenerative device from an elongated piece of porous metal having grooves formed therein to create points of detachment from the elongated piece.

In Example 35, the device or method of any one or any combination of Examples 1-34 can optionally be configured such that all elements or options recited are available to use or select from.

The claimed invention is:

1. A porous structure configured for use as one or more ridge augmentation devices for placement in a maxilla or a mandible of a patient, the porous structure comprising:
   a first side section;
   a second side section;
   a top section extending between and connecting the first side section and the second side section, the top section having a curved shape and defining a plurality of arch segments, an opening defined between each pair of adjacent arch segments and configured for receiving an implant, at least one of the arch segments having a detachment point, wherein the first side section, the second side section, and the top section being formed as a monolithic porous body; and
   for each detachment point, a first slot formed in the first side section and a second slot formed in the second side section, each of the first and second slots aligned with the corresponding detachment point, each of the first and second slots extending an entire height of the first and second side sections, respectively;
   wherein a selected portion of the monolithic porous body is detachable from a remaining portion of the monolithic porous body at any of the detachment points to decrease a longitudinal length of the monolithic porous body, the selected portion configured for use as a ridge augmentation device.

2. The porous structure of claim 1, wherein the porous structure has a curvature along at least a portion of an overall length of the porous structure.

3. The porous structure of claim 1, wherein the first side section includes a plurality of apertures, each aperture configured for receiving a fastener to attach the porous structure or a portion thereof to an alveolar ridge of a patient.

4. The porous structure of claim 1, wherein at least one of the arch segments has a different height than at least one of the other arch segments.

5. The porous structure of claim 1, wherein the porous structure is tantalum.

6. An apparatus configured for use as one or more ridge augmentation devices, the apparatus comprising:
   a plurality of units connected to one another, each of said plurality of units comprising:
   a first side section;
   a second side section; and
   a top section extending between and connecting the first and second side sections, the top section including an opening configured for receiving an implant, wherein the opening extends into at least one of a portion of the first side section and a portion of the second side section;
   wherein the first side sections of adjacent units are separated by a first slot and the second side sections of adjacent units are separated by a second slot, and a detachment point is formed in the top section between each pair of corresponding first and second slots,
   wherein the plurality of units are formed as a monolithic porous body, and
   wherein the detachment point allows a selected number of said plurality of units to be detached from the monolithic porous body for use as a ridge augmentation device.

7. The apparatus of claim 6, wherein the top section of each of said plurality of units has a curved shape.

8. The apparatus of claim 6, wherein the apparatus is formed of a porous metal.

9. The apparatus of claim 8, wherein the porous metal is tantalum.

10. The apparatus of claim 6, wherein at least one unit of the plurality of units includes an aperture in at least one of the first and second side sections.

11. The apparatus of claim 10, wherein the aperture is configured for receiving a fastener to attach the ridge augmentation device to an alveolar ridge of a patient.

* * * * *